(12) United States Patent
Eto et al.

(10) Patent No.: US 9,200,254 B2
(45) Date of Patent: Dec. 1, 2015

(54) METHOD FOR PRODUCING DIFFERENTIATED CELLS

(75) Inventors: Koji Eto, Kyoto (JP); Naoya Takayama, Kyoto (JP); Sou Nakamura, Tokyo (JP); Hiromitsu Nakauchi, Tokyo (JP)

(73) Assignee: The University of Tokyo, Tokyo (JP)

( * ) Notice: Subject to any disclaimer, the term of this patent is extended or adjusted under 35 U.S.C. 154(b) by 293 days.

(21) Appl. No.: 13/496,321

(22) PCT Filed: Sep. 15, 2010

(86) PCT No.: PCT/JP2010/065903
§ 371 (c)(1),
(2), (4) Date: May 21, 2012

(87) PCT Pub. No.: WO2011/034073
PCT Pub. Date: Mar. 24, 2011

(65) Prior Publication Data
US 2012/0238023 A1   Sep. 20, 2012

(30) Foreign Application Priority Data
Sep. 15, 2009 (JP) ................. 2009-213645

(51) Int. Cl.
*C12N 5/00* (2006.01)
*C12N 5/02* (2006.01)
*C12N 5/078* (2010.01)
*A61K 35/00* (2006.01)

(52) U.S. Cl.
CPC ............ *C12N 5/0644* (2013.01); *C12N 5/0641* (2013.01); *A61K 35/00* (2013.01); *C12N 2501/40* (2013.01); *C12N 2501/606* (2013.01); *C12N 2506/02* (2013.01); *C12N 2506/45* (2013.01)

(58) Field of Classification Search
CPC ................................................ C12N 5/0644
See application file for complete search history.

(56) References Cited

U.S. PATENT DOCUMENTS

| | | | |
|---|---|---|---|
| 572,333 A | 3/1888 | Levine et al. | |
| 5,686,576 A | 11/1997 | Avraham et al. | |
| 2007/0116691 A1 | 5/2007 | Cambier et al. | |
| 2010/0197016 A1 | 8/2010 | Nakauchi et al. | |

FOREIGN PATENT DOCUMENTS

| | | |
|---|---|---|
| EP | 1970446 A1 | 9/2008 |
| EP | 2096169 A1 | 9/2009 |
| JP | H06-508749 A | 10/1994 |
| JP | H10-513358 A | 12/1998 |
| JP | 2004-350601 A | 12/2004 |
| JP | 2006-061106 A | 3/2006 |
| JP | 2006-141356 A | 6/2006 |
| JP | 2009-511081 A | 3/2009 |
| WO | 2008/041370 A1 | 4/2008 |

OTHER PUBLICATIONS

Fujimoto et al. (2003) Production of functional platelets by differentiated embryonic stem (ES) cells in vitro. Blood 102: 4044-4051.*
Gulliksson (2003) Defining the optimal storage conditions for the long-term storage of platelets. Transfusion Medicine Reviews 17(3): 209-215.*
Jacobs et al. (1999) The oncogene and Polycomb-group gene bmi-1 regulates cell proliferation and senescence through the ink4a locus. Nature 397: 164-168.*
Li et al. (Aug. 2009) The Ink4/Arf locus is a barrier for iPS cell reprogramming. Nature 460: 1136-1141.*
Park et al. (2003) Bmi-1 is required for maintenance of adult self-renewing haematopoietic stem cells. Nature 423: 302-305.*
Rock et al. (1988) The effects of irradiation on platelet function. Transfusion 28(5): 451-455.*
Takayama et al. (Apr. 2008) Generation of functional platelets from human embryonic stem cells in vitro via ES-sacs, VEGF-promoted structures that concentrate hematopoietic progenitors. Blood 111: 5298-5306.*
Thompson et al. (1996) Deregulated expression of c-myc in megakaryocytes of transgenic mice increases megakaryopoiesis and decreases polyploidizaton. J. Biol. Chem. 271(38): 22976-22982.*
Utikal et al. (Aug. 2009) Immortalization eliminates a roadblock during cellular reprogramming into iPS cells. Nature 460:1145-1149.*
Kong (2011, Journal of Aging, 211:1-15.*
Wilson (2004, Genes and Development, 18:2747-2763.*
Mitjavila-Garcia, Development, 2002,129:2003-2013.*
Moon et al., "Reprogramming fibroblasts into induced pluripotent stem cells with Bmi1," Cell Research, 21: 1305-1315 (2011).
Extended Search Report issued in corresponding European Patent Application No. 10817186.9 dated Mar. 12, 2013.
Takayama et al., "Generation of functional platelets from human embryonic stem cells in vitro via ES-sacs, VEGF-promoted structures that concentrate hematopoietic progenitors," Blood, 111: 5298-5306 (2008).
Adbouh et al. (2009) BMI1 Sustains Human Glioblastoma Multiforme Stem Cell Renewal, J. Neurosci., 29:8884-8896.

* cited by examiner

*Primary Examiner* — Valarie Bertoglio
(74) *Attorney, Agent, or Firm* — Morgan, Lewis & Bockius LLP

(57) ABSTRACT

The present invention has an object of providing a method for producing specific cells by amplifying cells in a desired differentiation stage. The present invention provides a method for producing specific cells by inducing differentiation of cells, wherein an oncogene is forcibly expressed in cells in a desired differentiation stage to amplify the cells in the desired differentiation stage. The present invention also provides a method for producing specific cells, wherein oncogene-induced senescence (OIS) which is induced by the oncogene expressed in the cells in the desired differentiation stage is suppressed.

11 Claims, 20 Drawing Sheets

A

B

SEQUENCE LISTING

```
<160> NUMBER OF SEQ ID NOS: 4

<210> SEQ ID NO 1
<211> LENGTH: 1319
<212> TYPE: DNA
<213> ORGANISM: Homo sapiens

<400> SEQUENCE: 1
atgcccctca acgttagctt caccaacagg aactatgacc tcgactacga ctcggtgcag      60
ccgtatttct actgcgacga ggaggagaac ttctaccagc agcagcagca gagcgagctg     120
cagcccccgg cgcccagcga ggatatctgg aagaaattcg agctgctgcc caccccgccc     180
ctgtccccta gccgccgctc cgggctctgc tcgcctcct acgttgcggt cacacccttc      240
tcccttcggg gagacaacga cggcggtggc gggagcttct ccacgcccga ccagctggag     300
atggtgaccg agctgctggg aggagacatg gtgaaccaga gtttcatctg cgaccccggac    360 gacgagacct tcatcaaaaa catcatcatc caggactgta tgtggagcgg cttctcggcc     420
gccgccaagc tcgtctcaga gaagctggcc tcctaccagg ctgcgcgcaa agacagcggc     480
agcccgaacc ccgcccgcgg ccacagcgtc tgctccacct ccagcttgta cctgcaggat     540
ctgagcgccc ccgctcagag tgcatcgacc cctcggtggt cttcccctac cctctcaacg     600
acagcagctc gcccaagtcc tgcgcctcgc aagactccag cgccttctct ccgtcctcgg     660
attctctgct ctcctcgacg gagtcctccc cgcagggcag ccccgagccc ctggtgctcc     720
atgaggagac accgcccacc accagcagcg actctgagga ggaacaagaa gatgaggaag     780
aaatcgatgt tgtttctgtg gaaaagaggc aggctcctgg caaaaggtca gagtctggat     840
cacctcctgc tggaggccac agcaaacctc ctcacagccc actggtcctc aagaggtgcc     900
acgtctccac acatcagcac aactacgcag cgcctccctc cactcggaag gactatcctg     960
ctgccaagag ggtcaagttg gacagtgtca gagtcctgag acagatcagc aacaaccgaa    1020
aatgcaccag ccccaggtcc tcggacaccg aggagaatgt caagaggcga acacacaacg    1080
tcttggagcg ccagaggagg aacgagctaa aacggagctt ttttgccctg cgtgaccaga    1140
tcccggagtt ggaaaacaat gaaaaggccc ccaaggtagt tatccttaaa aaagccacag    1200
catacatcct gtccgtccaa gcagaggagc aaaagctcat ttctgaagag gacttgttgc    1260
ggaaacgacg agaacagttg aaacacaaac ttgaacagct acggaactct tgtgcgtaa     1319

<210> SEQ ID NO 2
<211> LENGTH: 981
<212> TYPE: DNA
<213> ORGANISM: Homo sapiens

<400> SEQUENCE: 2
atgcatcgaa caacgagaat caagatcact gagctaaatc cccacctgat gtgtgtgctt      60
tgtggagggt acttcattga tgccacaacc ataatagaat gtctacattc cttctgtaaa     120
```

```
acgtgtattg ttcgttacct ggagaccagc aagtattgtc ctatttgtga tgtccaagtt    180
cacaagacca gaccactact gaatataagg tcagataaaa ctctccaaga tattgtatac    240
aaattagttc cagggctttt caaaaatgaa atgaagagaa gaagggatt ttatgcagct    300 catccttctg ctgatgctgc caatggctct aatgaagata gaggagaggt tgcagatgaa    360
gataagagaa ttataactga tgatgagata ataagcttat ccattgaatt ctttgaccag    420
aacagattgg atcggaaagt aaacaaagac aaagagaaat ctaaggagga ggtgaatgat    480
aaaagatact tacgatgccc agcagcaatg actgtgatgc acttaagaaa gtttctcaga    540
agtaaaatgg acatacctaa tactttccag attgatgtca tgtatgagga ggaaccttta    600
aaggattatt atacactaat ggatattgcc tacatttata cctggagaag gaatggtcca    660
cttccattga atacagagt tcgacctact tgtaaaagaa tgaagatcag tcaccagaga    720
gatggactga caaatgctgg agaactggaa agtgactctg ggagtgacaa ggccaacagc    780
ccagcaggag gtattccctc cacctcttct tgtttgccta gccccagtac tccagtgcag    840
tctcctcatc cacagtttcc tcacatttcc agtactatga atggaaccag caacagcccc    900
agcggtaacc accaatcttc ttttgccaat agacctcgaa atcatcagt aaatgggtca    960 tcagcaactt cttctggttg a                                             981

<210> SEQ ID NO 3
<211> LENGTH: 1131
<212> TYPE: DNA
<213> ORGANISM: Homo sapiens

<400> SEQUENCE: 3
atgaattacg aatttgagcg agagattggt tttatcaata gccagccgtc gctcgctgag     60
tgcctgacat cttttcccc tgtcgctgat acatttcaaa gttcatcaat caagacctcg    120
acgctttcac actcgacact gattcctcct ccttttgagc agaccattcc cagcctgaac    180
cccggcagtc accctcgcca cggcgctggc ggccgcccca gccgagccc cgcgggcagc    240 cgcggcagcc cggtgcccgc cggcgccctg cagccgcccg agtaccctg gatgaaggag    300 aagaaggcgg ccaagaaaac cgcacttctg ccggccgccg ccgccgccgc caccgccgca    360
gccaccggcc ctgcttgcct cagccacaaa gaatccctgg aaatcgccga tggcagcggc    420
gggggatcgc ggcgcctgag aactgcttac accaacacac agcttctaga gctggaaaaa    480
gaatttcatt tcaacaagta cctttgcaga ccccgaaggg tggagattgc agcgctgctg    540
gatttgactg agagacaagt gaaagtgtgg tttcagaacc ggaggatgaa gcacaagagg    600
cagacccagt gcaaggaaaa ccaaaacagc gaagggaaat gtaaaagcct tgaggactcc    660
gagaaagtag aggaggacga ggaagagaag acgctctttg agcaagccct tagcgtctct    720
ggggcccttc tggagaggga aggctacact tttcagcaaa atgccctctc tcagcagcag    780
gctcccaatg gacacaatgg cgactccaa agtttcccag tctcgccttt aaccagcaat    840
gagaaaaatc tgaaacattt tcagcaccag tcacccactg ttcccaactg cttgtcaaca    900
atgggccaga actgtggagc tggcctaaac aatgacagtc ctgaggccct tgaggtcccc    960
tctttgcagg acttttagcgt tttctccaca gattcctgcc tgcagctttc agatgcagtt   1020
tcacccagtt tgccaggttc cctcgacagt cccgtagata tttcagctga cagcttagac   1080 tttttacag acacactcac cacaatcgac ttgcagcatc tgaattacta a              1131
```

```
<210> SEQ ID NO 4
<211> LENGTH: 702
<212> TYPE: DNA
<213> ORGANISM: Homo sapiens

<400> SEQUENCE: 4
atgtctcaga gcaaccggga gctggtggtt gactttctct cctacaagct ttcccagaaa      60
ggatacagct ggagtcagtt tagtgatgtg gaagagaaca ggactgaggc cccagaaggg     120
actgaatcgg agatggagac ccccagtgcc atcaatggca acccatcctg gcacctggca     180
gacagccccg cggtgaatgg agccactggc cacagcagca gtttggatgc ccgggaggtg     240
atccccatgg cagcagtaaa gcaagcgctg agggaggcag gcgacgagtt tgaactgcgg     300
taccggcggg cattcagtga cctgacatcc cagctccaca tcaccccagg gacagcatat     360
cagagctttg aacaggtagt gaatgaactc ttccgggatg gggtaaactg gggtcgcatt     420
gtggcctttt tctccttcgg cggggcactg tgcgtggaaa gcgtagacaa ggagatgcag     480
gtattggtga gtcggatcgc agcttggatg gccacttacc tgaatgacca cctagagcct     540
tggatccagg agaacggcgg ctgggatact tttgtggaac tctatgggaa caatgcagca     600
gccgagagcc gaaagggcca ggaacgcttc aaccgctggt tcctgacggg catgactgtg     660
gccggcgtgg ttctgctggg ctcactcttc agtcggaaat ga                        702
```

METHOD FOR PRODUCING DIFFERENTIATED CELLS

TECHNICAL FIELD

The present invention relates to a method for producing specific differentiated cells, and to a cell produced by the method. The present invention particularly relates to a method for producing differentiated blood cells, and to a blood cell produced by the method.

BACKGROUND ART

When specific cells are required for disease treatment, a sufficient amount of cells for achieving treatment goals need to be secured. However, it is difficult to obtain a sufficient amount of cells used for treatment from living organisms. Hence, methods such as a method of preparing target cells by inducing differentiation of their progenitor cells or the like ex vivo are being attempted.

In the case of treating blood-related diseases or performing surgical treatment, blood cells used for the treatment are required. Of blood cells, platelets essential for blood coagulation (hemostasis) and megakaryocytic cells responsible for producing proplatelets and further producing platelets are cells that are especially needed. In particular, platelets are in great demand in treatment of leukemia, bone marrow transplantation, anticancer therapy, and the like, and there is a significant need for stable supply of platelets. Methods used to secure platelets include not only a method of collecting blood from donors, but also a method of administering TPO-mimetic products, a method of differentiating megakaryocytic cells from umbilical cord blood or myeloid cells, and so on. Moreover, methods such as a method of preparing blood cells from hematopoietic stem cells or hematopoietic progenitor cells after amplifying these progenitor cells ex vivo are being attempted. Examples of reported methods include a method of establishing a hematopoietic stem cell line from mouse ES cells (Patent Document 1), a method of differentiating embryonic stem cells of primate animals into hematopoietic cells (Patent Document 2), and a method of easily and stably amplifying CD34-positive/CD38-negative cells that sustain undifferentiation of hematopoietic stem cells ex vivo (Patent Document 3).

When inducing differentiation of cells, pluripotent stem cells are extremely useful. Pluripotent stem cells such as ES cells and iPS cells can be used as a source for artificially producing blood cells such as platelets. In recent years, the establishment of iPS cells has contributed to increasing attention to the usefulness of pluripotent stem cells as an important source for cell therapy in regenerative medicine. For example, Takayama et al. have succeeded in inducing differentiation of human ES cells into megakaryocytic cells and platelets, creating a possibility of using platelets differentiated from ES cells as a source of platelet transfusion (Patent Document 4 and Non-Patent Document 1). The inventors have further established a method of preparing megakaryocytic cells and platelets from iPS cells, making it possible to solve a human leukocyte antigen (HLA) matching problem unavoidable in transfusion of ES cell-derived platelets. Though stable supply of a sufficient amount of platelets through blood donation has conventionally been difficult due to factors such as a chronic shortage of donors, this problem appears to be solvable by differentiation induction of platelets from ES cells or iPS cells. According to the hitherto proposed methods, however, only a small amount of platelets can be prepared from iPS cells or ES cells, and also a series of operations for production needs to be performed each time. It is therefore necessary to provide an improved, efficient method for ensuring quantitative stability of platelets.

Such a problem that needs to be solved in order to stably supply a sufficient amount of blood cells such as megakaryocytic cells and platelets can also be found in supply of other types of cells.

Thus, even in the case of preparing desired cells by differentiation induction of cells, it is still not easy to prepare progenitor cells of desired cells in large amount, so that at present there is difficulty in securing a sufficient amount of terminally-differentiated desired cells.

PRIOR ART DOCUMENTS

Patent Documents

Patent Document 1: Japanese Patent Application Laid-Open No. 2006-141356
Patent Document 2: Japanese Patent Application Laid-Open No. 2004-350601
Patent Document 3: Japanese Patent Application Laid-Open No. 2006-61106
Patent Document 4: WO2008/041370

Non-Patent Documents

Non-Patent Document 1: Takayama et al., Blood, 111: 5298-5306, 2008

SUMMARY OF THE INVENTION

Problems to be Solved by the Invention

Regarding blood cells, the present inventors have established the method of obtaining megakaryocytes and platelets from iPS cells. Upon clinically applying this method, however, the method needs to be improved so that megakaryocytes and platelets can be produced in large amount. It is also important to enable platelets to be speedily and stably supplied according to need, for realizing future clinical applications.

In view of the above-mentioned circumstances, the present invention provides a method for producing target cells through differentiation induction of cells, by increasing growth ability of cells in a desired differentiation stage and amplifying the cells to produce the target cells from the cells.

The present invention also provides a desired differentiated blood cell using this method. In particular, the present invention provides a megakaryocytic progenitor cell of high growth ability which is a blood cell serving as a source of mature megakaryocytic cells and platelets, and a method for producing such megakaryocytic progenitor cells.

Moreover, the present invention has an object of providing a method for producing mature megakaryocytic cells and platelets from the megakaryocytic progenitor cells stably in large amount, and a mature megakaryocytic cell produced by this method and a platelet differentiation-induced from the mature megakaryocytic cell.

The present invention also has an object of providing a method for producing erythroid cells and an erythroid cell produced by this method, given that stable supply of erythroid cells is equally required as with platelets.

The present invention further has an object of providing a long-term preservation method of megakaryocytic progenitor cells, i.e. cells in an immature state of mature megakaryocytic cells which are progenitor cells of platelets.

Means for solving the Problems

As a result of comparing megakaryocyte and platelet productivity of iPS cells established using four genes (OCT3/4, SOX2, KLF-4, c-MYC) and iPS cells established using the three genes (OCT3/4, SOX2, KLF-4) other than c-MYC, the present inventors have found that the iPS cells using the four genes produce megakaryocytes and platelets significantly more efficiently. The present inventors have also found that, though expression of the four genes introduced upon establishment is suppressed in iPS cells, reactivation of the c-MYC gene is induced with megakaryocytic differentiation, which is related to an increase in megakaryocyte production amount. The present inventors have further found that megakaryocytic progenitor cells without multi-polyploidization in which the c-MYC gene is forcibly expressed acquire high growth ability.

Typically, in the case where an oncogene such as c-MYC is overexpressed in cells, cell-cycle progression occurs and growth is activated. It is known that the cells perceive this growth as stress, and induce a defense response (oncogene-induced senescence: OIS) to suppress the stress, thereby suppressing excessive cell growth. The present inventors have noted this phenomenon, and further discovered a method for producing specific differentiated cells in large amount by regulating OIS of cells in a differentiation stage.

The present invention has been completed based on the above-mentioned findings.

That is, the present invention relates to the following (1) to (30).

(1) A method for producing specific cells by inducing differentiation of cells, wherein an oncogene is forcibly expressed in cells in a desired differentiation stage to amplify the cells in the desired differentiation stage.

(2) The method for producing specific cells according to the above-mentioned (1), wherein oncogene-induced senescence which is induced by the forced expression of the oncogene in the cells in the desired differentiation stage is suppressed.

(3) The method for producing specific cells according to the above-mentioned (1) or (2), wherein the suppression of the oncogene-induced senescence is achieved by expression of a polycomb gene.

(4) The method for producing specific cells according to any of the above-mentioned (1) to (3), wherein the cells in the desired differentiation stage are cells differentiation-induced from ES cells or iPS cells.

(5) The method for producing specific cells according to any of the above-mentioned (1) to (4), wherein an exogenous oncogene is introduced or an oncogene and a polycomb gene are introduced into the cells in the desired differentiation stage, and the introduced oncogene or the introduced oncogene and polycomb gene are forcibly expressed.

(6) The method for producing specific cells according to the above-mentioned (5), wherein the exogenous oncogene or the polycomb gene is introduced into progenitor cells of the cells in the desired differentiation stage, and the introduced oncogene or the introduced oncogene and polycomb gene are forcibly expressed.

(7) The method for producing specific cells according to the above-mentioned (5) or (6), wherein the oncogene and/or the polycomb gene are each operably linked to a downstream side of an inducible promoter, and the linked oncogene or the linked oncogene and polycomb gene are inducibly forcibly expressed.

(8) The method for producing specific cells according to any of the above-mentioned (5) to (7), wherein the expression of the oncogene or the expression of the oncogene and the polycomb gene in the cells in the desired differentiation stage is suppressed to promote differentiation of the cells in the desired differentiation stage.

(9) The method for producing specific cells according to the above-mentioned (8), wherein the suppression of the expression of the oncogene or the expression of the oncogene and the polycomb gene is achieved by operably linking the oncogene or the oncogene and the polycomb gene each to a downstream side of a suppressive promoter to thereby suppress the expression of the oncogene or the expression of the oncogene and the polycomb gene.

(10) The method for producing specific cells according to any of the above-mentioned (1) to (9), wherein the oncogene is a MYC family gene.

(11) The method for producing specific cells according to any of the above-mentioned (3) to (10), wherein the polycomb gene is BMI1.

(12) The method for producing specific cells according to any of the above-mentioned (6) to (11), wherein the progenitor cells of the cells in the desired differentiation stage are hematopoietic progenitor cells, the cells in the desired differentiation stage are megakaryocytic progenitor cells without multi-polyploidization, and the specific cells are mature megakaryocytic cells.

(13) The method for producing specific cells according to any of the above-mentioned (6) to (11), wherein the progenitor cells of the cells in the desired differentiation stage are hematopoietic progenitor cells, the cells in the desired differentiation stage are megakaryocytic progenitor cells without multi-polyploidization, and the specific cells are platelets.

(14) The method for producing specific cells according to the above-mentioned (12) or (13), wherein the hematopoietic progenitor cells are located in a net-like structure prepared from ES cells or iPS cells.

(15) A mature megakaryocytic cell which is a specific cell produced by the method according to the above-mentioned (12) or (14).

(16) A platelet which is a specific cell produced by the method according to the above-mentioned (13) or (14).

(17) A blood product comprising, as an active ingredient, the platelet according to the above-mentioned (16).

(18) A kit for producing the mature megakaryocytic cell according to the above-mentioned (15) or the platelet according to the above-mentioned (16).

(19) A blood cell in a desired differentiation stage, wherein an oncogene is forcibly expressed.

(20) The blood cell according to the above-mentioned (19), wherein a polycomb gene is also forcibly expressed.

(21) The blood cell according to the above-mentioned (19) or (20), wherein the blood cell in the desired differentiation stage is a cell differentiation-induced from an ES cell or an iPS cell.

(22) The blood cell according to any of the above-mentioned (19) to (21), wherein an exogenous oncogene is introduced or an oncogene and a polycomb gene are introduced into the blood cell in the desired differentiation stage, and the introduced oncogene or the introduced oncogene and polycomb gene are forcibly expressed.

(23) The blood cell according to the above-mentioned (22), wherein the exogenous oncogene or the polycomb gene is introduced into a progenitor cell of the blood cell in the desired differentiation stage, and the introduced oncogene or the introduced oncogene and polycomb gene are forcibly expressed.

(24) The blood cell according to the above-mentioned (22) or (23), wherein the oncogene and/or the polycomb gene are each operably linked to a downstream side of an inducible promoter, and the linked oncogene or the linked oncogene and polycomb gene are inducibly forcibly expressed.

(25) The blood cell according to any of the above-mentioned (19) to (24), wherein the oncogene is a MYC family gene.

(26) The blood cell according to any of the above-mentioned (20) to (25), wherein the polycomb gene is BMI1.

(27) The blood cell according to any of the above-mentioned (23) to (26), wherein the progenitor cell of the blood cell in the desired differentiation stage is a hematopoietic progenitor cell, and the blood cell in the desired differentiation stage is a pre-multinucleation megakaryocytic progenitor cell.

(28) The blood cell according to the above-mentioned (27), wherein the hematopoietic progenitor cell is located in a net-like structure prepared from an ES cell or an iPS cell.

(29) A frozen cellular composition comprising the blood cell according to any of the above-mentioned (19) to (28).

(30) A kit for producing the pre-multinucleation megakaryocytic progenitor cell which is the blood cell according to the above-mentioned (27) or (28).

Advantageous Effect of the Invention

According to the present invention, it is possible to amplify cells in a desired differentiation stage, and also produce specific cells differentiated from the amplified cells in large amount.

In addition, in the case of using the present invention for production of differentiated blood cells, it is possible to produce blood cells such as megakaryocytic cells and platelets from pluripotent stem cells stably in large amount.

Moreover, blood cells produced according to the present invention can be cryopreserved. For example, when megakaryocytic progenitor cells without multi-polyploidization are produced as blood cells, the cells can be cryopreserved. Hence, it is possible to supply mature megakaryocytic cells and platelets derived from the same source of megakaryocytic progenitor cells.

In particular, in the method according to the present invention, megakaryocytic progenitor cells without multi-polyploidization (progenitor cells of mature megakaryocytic cells) that can be cryopreserved can be prepared from iPS cells in large amount. By using these megakaryocytic progenitor cells without multi-polyploidization as a source, it is possible to produce and supply a sufficient amount of platelets for repeated blood transfusion while avoiding the HLA matching problem.

Furthermore, according to the present invention, a method for stably supplying erythroid cells in vitro is provided.

MODE FOR CARRYING OUT THE INVENTION

Figure 1:
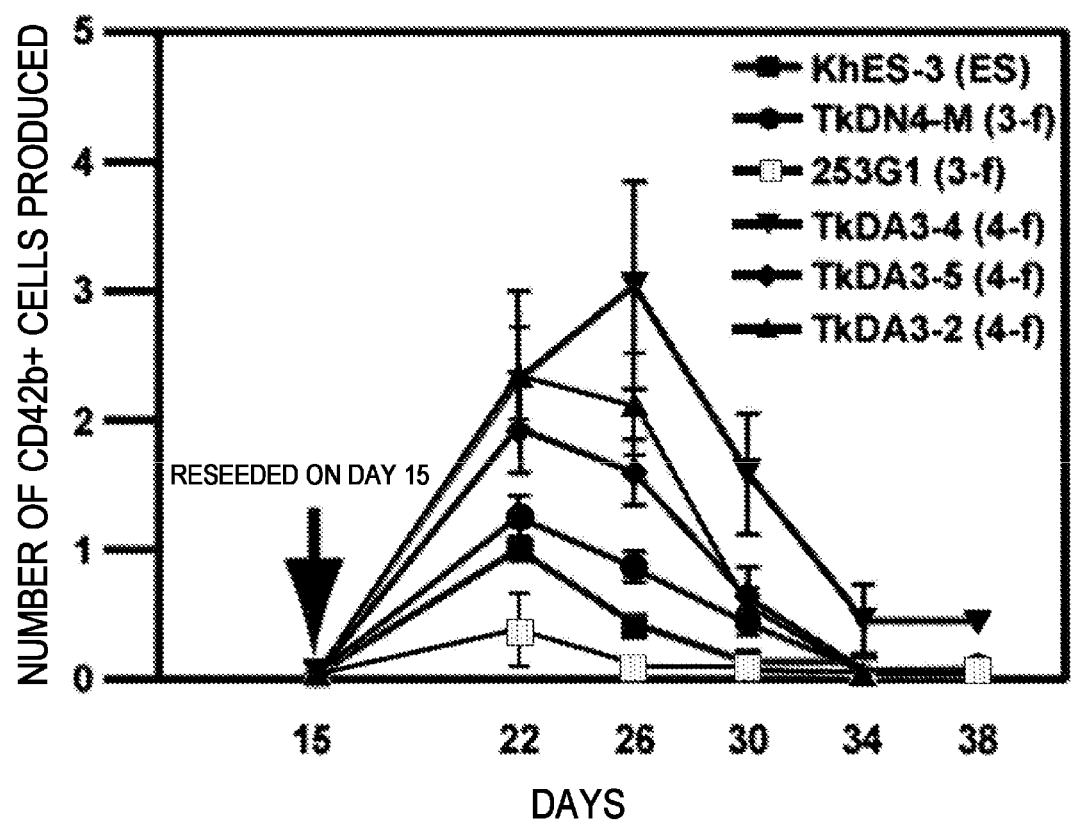
FIG. 1 is a graph for comparison of the numbers of megakaryocytic cells produced from four-factor iPS cells and three-factor iPS cells. The vertical axis represents the number of CD42b-positive megakaryocytic cells derived from each cell, where the number of ES cell-derived CD42b-positive megakaryocytic cells on day 22 of culture is set to 1. The horizontal axis represents the number of days after initiation of culture of iPS cells and ES cells. "3-f" indicates a three-factor iPS cell-derived cell line, "4-f" indicates a four-factor iPS cell-derived cell line, and "ES" indicates ES cells.

One embodiment of the present invention is a method for producing specific cells by inducing differentiation of cells that serve as a source, wherein an oncogene is forcibly expressed in cells in a desired differentiation stage within a process of differentiation from the cells that serve as the source into the specific cells, in order to amplify (or grow) the cells in the desired differentiation stage.

Here, "cells that serve as a source" correspond to progenitor cells of target cells (specific cells) obtained by differentiation induction, and may be any cells retaining differentiation ability other than terminally-differentiated cells. For example, "cells that serve as a source" may be completely-undifferentiated pluripotent stem cells, or cells that are differentiated to some extent but still retain differentiation ability (e.g. hematopoietic progenitor cells of blood cells). Moreover, "specific cells" produced in this embodiment are cells other than completely-undifferentiated cells (e.g. pluripotent stem cells), and may be cells having an undifferentiated state to some extent. That is, "specific cells" are cells that emerge between a complete undifferentiated stage to a terminal differentiated stage, except completely-undifferentiated cells. When taking blood cells as an example, "specific cells" in this embodiment are mature megakaryocytic cells, platelets, erythroid cells, or the like.

In this embodiment, "cells in a differentiation stage" to be amplified (or grown) are cells that emerge between the complete undifferentiated stage to the terminal differentiated stage, i.e. cells other than cells in the complete undifferentiated stage (e.g. pluripotent stem cells, etc.) and cells in the terminal differentiated stage. When taking blood cells as an example, "cells in a differentiation stage" in this embodiment are hematopoietic progenitor cells or megakaryocytic progenitor cells without multi-polyploidization, which are progenitor cells of mature megakaryocytic cells. For instance, cells induced from pluripotent stem cells such as ES cells or iPS cells may be used as "cells in a differentiation stage".

ES cells used in the present invention are not particularly limited. Typically, blastocyst stage fertilized eggs are co-cultured with feeder cells, grown inner cell mass-derived cells are separated, and subculture is further repeated, eventually enabling establishment of an ES cell line. Thus, ES cells are usually obtained from fertilized eggs. Alternatively, ES cell-like cells that are obtained from, for example, adipose tissues, chorionic villi, amniotic fluids, placentas, testicular cells, and the like other than fertilized eggs, have characteristics similar to ES cells, and exhibit pluripotency may be used.

iPS cells used in the present invention may be cells of any origins, as long as they are cells acquiring pluripotency equivalent to that of ES cells as a result of introduction of several types of transcription factor (hereafter referred to as "pluripotency factor") genes for providing pluripotency into somatic cells (e.g. fibroblast cells, blood cells, etc.). Many factors have already been reported as pluripotency factors.

Examples of the factors include Oct family (e.g. Oct3/4), SOX family (e.g. SOX2, SOX1, SOX3, SOX15, SOX 17, etc.), Klf family (e.g. Klf4, Klf2, etc.), MYC family (e.g. c-MYC, N-MYC, L-MYC, etc.), NANOG, LIN28, and the like, though the present invention is not limited to such. iPS cell establishment methods are described in many documents which can be referenced to (see, for example, Takahashi et al., Cell 2006, 126: 663-676; Okita et al., Nature 2007, 448: 313-317; Wernig et al., Nature 2007, 448: 318-324; Maherali et al., Cell Stem Cell 2007, 1: 55-70; Park et al., Nature 2007, 451: 141-146; Nakagawa et al., Nat Biotechnol 2008, 26: 101-106; Wernig et al., Cell Stem Cell 2008, 10: 10-12; Yu et al., Science 2007, 318: 1917-1920; Takahashi et al., Cell 2007, 131: 861-872; Stadtfeld et al., Science 2008, 322: 945-949, etc.).

An oncogene used in the present invention is a gene that induces canceration of a cell where the gene resides. Examples of the gene include MYC family genes, SRC family genes, RAS family genes, RAF family genes, protein kinase family genes such as c-Kit, PDGFR, and Abl, and the like, though the present invention is not limited to such.

In the present invention, forced expression of the oncogene or the below-mentioned polycomb gene in the cells in the desired differentiation stage may be achieved in a manner that introduces the oncogene or the polycomb gene into the cells in the desired differentiation stage and forcibly expresses the gene, in a manner that introduces the gene into progenitor cells of the cells in the desired differentiation stage, forcibly expresses the gene, and proceeds with differentiation while sustaining the expression so that the forced expression state of the gene is maintained in the cells in the desired differentiation stage, or in a manner that introduces the gene in progenitor cells of the cells in the desired differentiation stage and, when the progenitor cells are differentiated into the cells in the desired differentiation stage, induces the forced expression of the gene. For example, in the case of amplifying megakaryocytic progenitor cells without multi-polyploidization as the cells in the desired differentiation stage, the oncogene or the polycomb gene may be introduced into hematopoietic progenitor cells (described later) which are in a progenitor stage of the megakaryocytic progenitor cells without multi-polyploidization, and forcibly expressed. In the case of forcibly expressing both the oncogene and the polycomb gene in the cells in the desired differentiation stage, the oncogene and the polycomb gene may be introduced into the cells simultaneously or at different timings.

The embodiment of the present invention also includes a method for amplifying (or growing) the cells in the desired differentiation stage, wherein oncogene-induced senescence which is induced by the forced expression of oncogene in the cells in the desired differentiation stage is suppressed.

Oncogene-induced senescence (OIS) is stress-induced senescence induced by abnormal growth stimuli and the like by an oncogene such as RAS or MYC. When an oncogene product is excessively expressed in cells, expression of a tumor suppressor gene product such as p16 or p19 coded at a CDKN2a (INK4a/ARF) locus is induced. This induces senescence of cells and apoptosis, causing a decrease in cell growth activity. It is therefore expected that high cell growth ability can be maintained by avoiding OIS induced by the oncogene.

For example, oncogene-induced senescence can be suppressed by expressing the polycomb gene in the cells in which the oncogene is expressed. The polycomb gene (polycomb group: PcG) negatively regulates the CDKN2a (INK4a/ARF) locus, and functions to avoid senescence (see, for example, Oguro et al., "Regulation of stem cell senescence by polycomb group protein complex", Regenerative Medicine, vol. 6, no. 4, pp. 26-32; Jseus et al., Nature Reviews Molecular Cell Biology, vol. 7, pp. 667-677, 2006; Proc. Natl. Acad. Sci. USA, vol. 100, pp. 211-216, 2003). Accordingly, by expressing the polycomb gene in the cells in addition to the oncogene such as a MYC family gene, oncogene-induced senescence can be avoided and the cell growth effect of the oncogene product can be further enhanced.

Examples of the polycomb group gene used in the present invention include BMI1, Mell 8, Ring1a/b, Phc1/2/3, Cbx2/4/6/7/8, Ezh2, Eed, Suz12, HDAC, Dnmt1/3a/3b, and the like. An especially preferable polycomb group gene is the BMI1 gene.

Oncogene-induced senescence can also be suppressed by expression of the HOXA2 gene or the BCLXL gene.

In order to forcibly express the oncogene and the polycomb gene in the cells, any method well known to a person skilled in the art may be employed. For instance, an exogenous oncogene or an exogenous polycomb gene may be introduced into the cells through the use of a gene introduction system such as a lentivirus or a retrovirus, and expressed. In the case of expressing the gene by a viral gene introduction vector, the gene may be operably linked to a downstream side of an appropriate promoter, which is then inserted into the gene introduction vector and introduced into the cells to express the target gene. Here, the "operable" linkage means that the promoter and the target gene are linked so that the target gene is cis-dominated by the promoter and desired expression of the target gene is realized. In the embodiment of the present invention, for example, the target gene may be constitutively expressed using a CMV promoter, an EF1 promoter, or the like. As an alternative, an appropriate promoter (inducible promoter) may be placed under control of an element whose activity is regulated by a trans factor, e.g. a drug response element such as tetracycline response element, where the target gene is inducibly expressed by regulation through drug addition or the like. As such a drug-based gene expression system, an appropriate system can be easily selected by a person skilled in the art in order to realize desired expression regulation of the oncogene or the polycomb gene. A commercially available kit for such an expression system may be purchased and put to use. Though the oncogene and the polycomb gene, which are the target genes in expression regulation, may be inserted into separate vectors, it is more preferable to insert the oncogene and the polycomb gene into the same vector.

This embodiment also includes a method for producing the target specific cells, by further inducing differentiation of the cells in the desired differentiation stage in which the oncogene or the oncogene and the polycomb gene are expressed. To further induce the differentiation of the cells in the desired differentiation stage, the cells in the differentiation stage may be cultured under culture conditions (conditions such as a culture medium and a culture temperature) suitable for the differentiation induction, and also the expression of the oncogene or the polycomb gene in the cells in the differentiation stage may be suppressively regulated according to need. In this case, the expression of the oncogene or the polycomb gene may be suppressed, for example, by clearing the induction of the gene expression induced by the above-mentioned inducible expression system, through drug removal or the like. Alternatively, the oncogene or the polycomb gene may be operably linked to a suppressive promoter that performs constitutive expression regulation in the absence of a drug or the like and performs suppressive expression regulation in the presence of the drug or the like, to suppressively regulate the expression of the gene. Moreover, the introduced oncogene or polycomb gene may be removed using a Cre/Lox system or the like, thereby suppressively regulating the expression of the gene. A commercially available kit and the like may be used as appropriate, in order to suppressively regulate the expression of the oncogene or the polycomb gene.

This embodiment also includes a method for amplifying (growing) megakaryocytic progenitor cells without multi-polyploidization as the cells in the desired differentiation stage and producing, as the specific cells, mature megakaryocytic cells from the megakaryocytic progenitor cells without multi-polyploidization. Here, in the case of forcibly expressing the oncogene or the oncogene and the polycomb gene in the megakaryocytic progenitor cells without multi-polyploidization, it is preferable to express the oncogene or the oncogene and the polycomb gene in hematopoietic progenitor cells in a progenitor stage of the megakaryocytic progenitor cells without multi-polyploidization.

In this description, "megakaryocytic progenitor cells without multi-polyploidization" are megakaryocyte-specific marker CD41a-positive/CD42a-positive/CD42b-positive mononuclear or binuclear cells that have not undergone nuclear polyploidization. On the other hand, "hematopoietic progenitor cells" are hematopoietic cells characterized as CD34+ cells (CD34-positive cells), which may be ES cell- or iPS cell-derived cells as an example, and preferably cells obtained from a net-like structure (also referred to as ES-sac or iPS-sac) prepared from ES cells or iPS cells (in particular, cells immediately after separation from the net-like structure). Here, "net-like structure" prepared from ES cells or iPS cells is an ES cell- or iPS cell-derived three-dimensional sac-like (containing a space therein) structure that is formed by an endothelial cell population or the like and contains hematopoietic progenitor cells inside. For details on net-like structures, see, for example, Takayama et al., Blood 2008, 111: 5298-5306.

Cell culture conditions suitable for preparing the net-like structure from human ES cells or human iPS cells differ depending on the type of ES cells or iPS cells used. However, as an example, a culture medium may be IMDM to which FBS in a final concentration of 15% is added. Other serum-free medium may also be used with growth factors, supplements, and the like being added as appropriate. Moreover, preferably 0 to 100 ng/ml and more preferably approximately 20 ng/ml VEGF is added in order to efficiently form the net-like structure. A culture environment differs depending on the type of ES cells or iPS cells used. However, as an example, conditions of 5% $CO_2$ and 36 to 38° C. and preferably 37° C. may be used. Though a culture period until the net-like structure is formed differs depending on the type of ES cells or iPS cells, the presence of the net-like structure can be recognized on approximately days 14 to 16 after seeding onto feeder cells.

The formed net-like structure has a follicular structure, and contains hematopoietic progenitor cells in a concentrated state. The hematopoietic progenitor cells inside the net-like structure can be separated by physical means, such as by passing through a sterilized sieve instrument (e.g. a cell strainer, etc.). The hematopoietic progenitor cells obtained in such a way can be used in the present invention.

Though the oncogene forcibly expressed in the hematopoietic progenitor cells may be any of the above-mentioned oncogenes, a MYC family gene is especially preferable. Examples of the MYC family gene include c-MYC, N-MYC, L-MYC, and the like. Of these genes, c-MYC is especially preferable. Though the polycomb gene forcibly expressed in the hematopoietic progenitor cells may be any of the above-mentioned polycomb genes, the BMI1 gene is especially preferable.

The hematopoietic progenitor cells expressing the oncogene such as the MYC family gene and the polycomb gene such as the BMI1 gene are cultured under conditions that any one of or a combination of at least two of SCF (10 to 200 ng/ml, e.g. 100 ng/ml), TPO (10 to 200 ng/ml, e.g. 40 ng/ml), FL (10 to 200 ng/ml, e.g. 100 ng/ml), VEGF (10 to 200 ng/ml, e.g. 40 ng/ml), and the like is added, and become megakaryocytic progenitor cells without multi-polyploidization that have acquired high growth ability on, for example, approximately days 4 to 7 after gene introduction. The megakaryocytic progenitor cells without multi-polyploidization obtained in this way sustain their cell growth at least for approximately 30 to 50 days, preferably for approximately 50 to 60 days or more, and more preferably for 60 days or more, and amplify in the number of cells to approximately $1.0 \times 10^4$ times or more, preferably approximately $1.0 \times 10^5$ times or more, and more preferably approximately $1.0 \times 10^6$ times or more the number of cells when introducing the c-MYC gene and the BMI1 gene (see, for example, FIG. 12).

The present invention also includes a method for producing mature megakaryocytic cells and further producing platelets by culturing, under conditions suitable for differentiation induction of blood cells, the megakaryocytic progenitor cells without multi-polyploidization produced by the method according to the present invention. The conditions suitable for differentiation induction of blood cells are, for example, that any one of or a combination of at least two of TPO, IL-1α, IL-3, IL-4, IL-5, IL-6, IL-9, IL-11, EPO, GM-CSF, SCF, G-CSF, Flt3 ligand, heparin, and the like is added. In the case of differentiation induction of the mature megakaryocytic cells and the platelets, for example, culture may be performed for approximately 7 to 15 days in the presence of TPO (10 to 200 ng/ml, preferably approximately 100 ng/ml) or in the presence of TPO (10 to 200 ng/ml, preferably approximately 100 ng/ml), SCF (10 to 200 ng/ml, preferably approximately 50 ng/ml), and heparin (10 to 100 U/ml, preferably approximately 25 U/ml). Any culture environment suitable for differentiation induction of blood cells in vitro is applicable. As an example, culture is performed under conditions of 5% $CO_2$ and 36 to 38° C. and preferably 37° C.

In the case of inducing differentiation of the megakaryocytic progenitor cells without multi-polyploidization, which have acquired high growth ability as a result of introduction of the oncogene and the polycomb gene, into mature megakaryocytic cells, platelets, and the like, the expression of the oncogene and the polycomb gene may be suppressively regulated according to need, as mentioned earlier.

Another embodiment of the present invention is a method for producing erythroid cells, wherein the erythroid cells are produced by forcibly expressing an oncogene and the HOXA2 gene or the BCLXL gene in hematopoietic progenitor cells to amplify erythroid progenitor cells. In more detail, this embodiment relates to a method whereby an oncogene such as a MYC family gene is forcibly expressed in erythroid progenitor cells which are cells in a desired differentiation stage, and oncogene-induced senescence induced as a result is suppressed by expression of the HOXA2 gene or the BCLXL gene to amplify the erythroid progenitor cells, thereby producing erythroid cells as specific cells. This embodiment is based on the findings that, as a result of introducing dozens of types of hematopoietic transcription factors and anti-apoptosis-associated genes into hematopoietic progenitor cells together with MYC as an oncogene and performing a screening, HOXA2 or BCLXL induces growth of erythroid progenitor cells.

Though any oncogene may be used as the oncogene forcibly expressed in the hematopoietic progenitor cells as mentioned earlier, a MYC family gene is preferable, and the c-MYC gene is especially preferable.

In this description, "erythroid progenitor cells" are erythrocyte-specific molecule Glycophorin A-positive pre-enucleation cells.

The hematopoietic progenitor cells expressing the oncogene such as the MYC family gene and the HOXA2 gene or the BCLXL gene are cultured under conditions that any one of or a combination of at least two of SCF (10 to 200 ng/ml, e.g. 100 ng/ml), TPO (10 to 200 ng/ml, e.g. 40 ng/ml), FL (10 to 200 ng/ml, e.g. 100 ng/ml), VEGF (10 to 200 ng/ml, e.g. 40 ng/ml), EPO (1 to 100 U/ml, e.g. 6 U/ml), and the like is added, and become pre-enucleation erythroid progenitor cells that have acquired high growth ability on, for example, approximately days 4 to 7 after gene introduction.

Conditions suitable for differentiation induction of mature erythroid cells via the erythroid progenitor cells obtained from the hematopoietic progenitor cells expressing the MYC family gene and the BCLXL gene or the HOXA2 gene are, for example, that any one of or a combination of at least two of TPO, IL-1α, IL-3, IL-4, IL-5, IL-6, IL-9, IL-11, EPO, GM-CSF, SCF, G-CSF, Flt3 ligand, heparin, and the like is added. In particular, the erythroid cells can be cultured for approximately 7 to 15 days in the presence of EPO (2 to 100 U/ml, preferably approximately 10 U/ml) or in the presence of EPO (2 to 100 U/ml, preferably approximately 10 U/ml) and SCF (10 to 200 ng/ml, preferably approximately 50 ng/ml). Any culture environment suitable for differentiation induction of blood cells in vitro is applicable. As an example, culture is performed under conditions of 5% $CO_2$ and 36 to 38° C. and preferably 37° C.

Another embodiment of the present invention includes blood cells in a desired differentiation stage in which an oncogene is forcibly expressed. Here, the oncogene may be any of the above-mentioned oncogenes. For example, a MYC family gene or the like is applicable, and the c-MYC gene is especially preferable. Moreover, "blood cells in a differentiation stage" are blood cells that emerge between a complete undifferentiated stage to a terminal differentiated stage, i.e. blood cells other than cells in the complete undifferentiated stage and cells in the terminal differentiated stage. For instance, "blood cells in a differentiation stage" in this embodiment are megakaryocytic progenitor cells without multi-polyploidization or the like. As such blood cells in the differentiation stage, cells induced from ES cells or iPS cells may be used, as an example. Especially, blood cells obtained from a net-like structure (also referred to as ES-sac or iPS-sac) prepared from ES cells or iPS cells (in particular, cells immediately after separation from the net-like structure) are preferable. This embodiment also includes blood cells in a differentiation stage in which not only the oncogene but also the above-mentioned polycomb gene is forcibly expressed. The forced expression of the oncogene and the polycomb gene may be induced using an inducible promoter or the like, as mentioned above.

The forced expression of the oncogene or the polycomb gene in the cells in the desired differentiation stage may be achieved in a manner that introduces the oncogene or the polycomb gene into the blood cells in the desired differentiation stage and forcibly expresses the gene, in a manner that introduces the gene into progenitor cells of the blood cells in the desired differentiation stage, forcibly expresses the gene, and proceeds with differentiation while sustaining the expression so that the forced expression of the gene is maintained in the blood cells in the desired differentiation stage, or in a manner that introduces the gene into progenitor cells of the blood cells in the desired differentiation stage and, when the progenitor cells are differentiated into the blood cells in the desired differentiation stage, induces the forced expression of the gene. For example, in the case of amplifying megakaryocytic progenitor cells without multi-polyploidization as the blood cells in the desired differentiation stage, the oncogene or the polycomb gene may be introduced into hematopoietic progenitor cells which are in a progenitor stage of the megakaryocytic progenitor cells without multi-polyploidization, and forcibly expressed.

The blood cells such as the megakaryocytic progenitor cells without multi-polyploidization in this embodiment have a freeze-thaw resistance and retain the cell growth ability and the differentiation ability even when cryopreserved and then thawed. This allows the blood cells to be frozen and thawed according to need, thereby producing differentiation-induced blood cells. The use of these cells eliminates the need to perform a series of operations for producing blood cells such as platelets from ES cells or iPS cells from the beginning. That is, by preparing, as raw materials, a large amount of blood cells in which the oncogene or the oncogene and the polycomb gene are forcibly expressed according to the present invention and cryopreserving the blood cells according to need, the manufacturing process can be rationalized and improved in efficiency. Hence, a mechanism capable of speedily supplying various blood cells such as platelets can be established.

In the case of producing a frozen cellular composition using the blood cells such as the megakaryocytic progenitor cells without multi-polyploidization according to the present invention, the frozen cellular composition may comprise the blood cells such as the megakaryocytic progenitor cells without multi-polyploidization and a cryopreservation solution. An additive and the like may also be comprised in the composition as needed.

For instance, a freeze solution containing DMSO may be used as the cryopreservation solution. Specific examples include Cell Banker (Nippon Zenyaku Kogyo Co., Ltd.), Bambanker (Nippon Genetics Co., Ltd.), TC-Protector (DS Pharma Biomedical Co., Ltd.), and albumin-supplemented CP-1 (Kyokuto Pharmaceutical Industrial Co., Ltd.).

The MYC family gene, the polycomb gene (e.g. the BMI1 gene), the HOXA2 gene, and the BCLXL gene used in the present invention include not only genes whose cDNA sequences have already been published, but also homologs identified by conventional techniques based on homology of these well known cDNA sequences. A homolog of the c-MYC gene among the MYC family genes is a gene whose cDNA sequence consists of, for example, a substantially identical sequence to a nucleic acid sequence set forth in SEQ ID NO: 1. Here, cDNA consisting of a substantially identical sequence to a nucleic acid sequence set forth in SEQ ID NO: 1 is either DNA consisting of a sequence having identity of approximately 60% or more, preferably approximately 70% or more, more preferably approximately 80%, 81%, 82%, 83%, 84%, 85%, 86%, 87%, 88%, 89%, 90%, 91%, 92%, 93%, 94%, 95%, 96%, 97%, or 98%, and most preferably approximately 99% with DNA consisting of the sequence set forth in SEQ ID NO: 1, or DNA that can hybridize to DNA consisting of a complementary sequence of the nucleic acid sequence set forth in SEQ ID NO: 1 under stringent conditions, where protein coded by such DNA contributes to amplification of the cells in the differentiation stage such as the megakaryocytic progenitor cells without multi-polyploidization.

A homolog of the BMI1 gene used in the present invention is a gene whose cDNA sequence consists of, for example, a substantially identical sequence to a nucleic acid sequence set forth in SEQ ID NO: 2. Here, cDNA consisting of a substantially identical sequence to a nucleic acid sequence set forth in SEQ ID NO: 2 is either DNA consisting of a sequence having identity of approximately 60% or more, preferably approximately 70% or more, more preferably approximately 80%, 81%, 82%, 83%, 84%, 85%, 86%, 87%, 88%, 89%, 90%, 91%, 92%, 93%, 94%, 95%, 96%, 97%, or 98%, and most preferably approximately 99% with DNA consisting of the sequence set forth in SEQ ID NO: 2, or DNA that can hybridize to DNA consisting of a complementary sequence of the nucleic acid sequence set forth in SEQ ID NO: 2 under stringent conditions, where protein coded by such DNA suppresses oncogene-induced senescence induced in the cells in which the oncogene such as the MYC family gene is expressed, thereby facilitating amplification of the cells.

The HOXA2 gene or the BCXL gene used in the present invention is a gene whose cDNA sequence consists of, for example, a substantially identical sequence to a nucleic acid sequence set forth in SEQ ID NO: 3 or 4. Here, cDNA consisting of a substantially identical sequence to a nucleic acid sequence set forth in SEQ ID NO: 3 or 4 is either DNA consisting of a sequence having identity of approximately 60% or more, preferably approximately 70% or more, more preferably approximately 80%, 81%, 82%, 83%, 84%, 85%, 86%, 87%, 88%, 89%, 90%, 91%, 92%, 93%, 94%, 95%, 96%, 97%, or 98%, and most preferably approximately 99% with DNA consisting of the sequence set forth in SEQ ID NO: 3 or 4, or DNA that can hybridize to DNA consisting of a complementary sequence of the nucleic acid sequence set forth in SEQ ID NO: 3 or 4 under stringent conditions, where protein coded by such DNA has an effect of causing the erythroid progenitor cells to grow.

The stringent conditions mentioned here are hybridization conditions easily determined by a person skilled in the art, and are empirical experimental conditions that typically depend on a probe length, a washing temperature, and a salt concentration. Usually, a temperature for proper annealing is higher when a longer probe is used, and lower when a shorter probe is used. Hybrid formation typically depends on reannealing ability in an environment where a complementary strand is slightly lower in temperature than its melting point. In detail, low stringent conditions are, for example, conditions that washing is performed in a solution of 0.1×SSC, 0.1% SDS under temperature conditions of 37° C. to 42° C. in a filter washing stage after hybridization. High stringent conditions are, for example, conditions that washing is performed in a solution of 5×SSC, 0.1% SDS at 65° C. in the washing stage. Polynucleotide of higher identity can be obtained by further enhancing the stringent conditions.

The embodiment of the present invention further includes a kit for producing cells in a desired differentiation stage (e.g. megakaryocytic progenitor cells without multi-polyploidization or erythroid progenitor cells) or finally-produced specific cells (e.g. megakaryocytic cells, platelets, or erythroid cells). The kit comprises reagents and expression vectors and the like necessary for expressing the oncogene, the polycomb gene, the BCLXL gene, the HOXA2 gene, or the like in cells, and also comprises a culture medium for cell culture, serum, supplements such as growth factors (e.g. TPO, EPO, SCF, heparin, IL-6, IL-11, etc.), antibiotics, and so on. In addition, for example in the case of using ES cell- or iPS cell-derived cells, the kit further comprises antibodies for confirmation of markers for identifying a net-like structure prepared from these cells (e.g. antibodies against Flk1, CD31, CD34, UEA-I lectin, etc.). The reagents, the antibodies, and the like comprised in the kit are supplied in any type of vessel in which components effectively sustain their activity over a long period of time without being adsorbed on or degenerated by the material of the vessel.

The platelets and the erythroid cells produced according to the present invention may be stably supplied in drug product form. The platelets produced by the method according to the present invention can be prepared by recovering a fraction of a culture solution in which platelets released from megakaryocytic cells are abundant, and removing blood cell components other than platelets, such as megakaryocytic cells, through the use of a leukocyte-removing filter (e.g. commercially available from Terumo Corporation, Asahi Kasei Medical Co., Ltd., etc.) or the like. Upon preparing a blood product, other components contributing to stabilization of platelets or erythroid cells may be comprised in the blood product. For such components contributing to stabilization, a method well known to a person skilled in the art may be selected.

In more detail, the obtained platelets may be formulated by the following method, as an example.

An ACD-A solution and FFP (fresh frozen plasma, which is prepared from whole blood obtained through blood donation and comprises all components other than blood components, such as albumin and a coagulation factor) are prepared at a ratio of 1:10, and preserved while shaking at 20 to 24° C. after irradiation of 15 to 50 Gy. The ACD-A solution is prepared by mixing 22 g sodium citrate, 8 g citric acid, and 22 g glucose with water for injection to a total amount of 1 L.

In the case of using the above-mentioned method, it is desirable that a platelet concentration is approximately $1 \times 10^9$ platelets/ml, as an example.

Moreover, addition of GM6001 (a broad-range hydroxamic acid-based metalloprotease inhibitor) (Calbiochem, La Jolla, Calif., USA) enables prevention of inactivation caused by a cleavage of a platelet functional molecule GPIb-V-IX or GPVI that occurs during cryopreservation or room temperature preservation. The present inventors have confirmed that inactivation can be prevented for mouse ES cell-derived platelets by this method. For information on a mechanism underlying this platelet inactivation using human platelets, see Bergmeier, W. et al., Cir Res 95: 677-683, 2004, and Gardiner, E E. et al., J Thrombosis and Haemostasis, 5: 1530-1537, 2007.

As a material of a vessel for containing a drug product comprising platelets, it is preferable not to use a material, such as glass, that activates platelets.

On the other hand, the erythroid cells may be formulated in the following manner. In more detail, the obtained erythrocytes may be formulated by the following method, as an example.

A MAP solution (whose composition is described below) is added to an erythrocyte concentrate obtained by concentrating a culture supernatant after centrifugation and prepared, and preserved at 2 to 6° C. after irradiation of 15 to 50 Gy.

In the case of using the above-mentioned method, it is desirable that an erythrocyte concentration is approximately $1 \times 10^{10}$ erythrocytes/ml, as an example. For the obtained erythrocytes, for instance, a loading solution for erythrocyte preservation (MAP solution) prepared by dissolving D-mannitol (14.57 g), adenine (0.14 g), sodium dihydrogen phosphate crystal (0.94 g), sodium citrate (1.50 g), citric acid (0.20 g), glucose (7.21 g), and sodium chloride (4.97 g) with water for injection to a total amount of 1000 ml may be used.

Any other well known method suitable for erythrocyte formulation may be easily selected by a person skilled in the art as appropriate.

The present invention further includes a frozen composition of blood cells according to the present invention. The composition may comprise not only the blood cells but also a culture medium necessary for preserving the blood cells, a buffer solution, and DMSO, glycerol, and the like for protecting the cells upon freezing. The composition may further comprise any other normal substances necessary for freezing the cells. In the case where a commercially available cell freeze reagent is used, the composition may comprise substances contained in the reagent.

The origin of "cells" described in this description may be humans or non-human animals (e.g. mice, rats, cows, horses, pigs, sheep, monkeys, dogs, cats, birds, etc.). Though the origin is not particularly limited, human-derived cells are especially preferable.

The present invention is described in more detail by way of examples below, though these examples are not intended to limit the scope of the present invention.

EXAMPLES

1. Comparison of Megakaryocyte Production Efficiency from Four-Factor iPS Cells and Three-Factor iPS Cells The numbers of megakaryocytic cells produced from iPS cells (TkDA3-2, TkDA3-4, and TkDA3-5) established using four genes (OCT3/4, SOX2, KLF-4, c-MYC), iPS cells (253G1 (provided by Prof. Shinya Yamanaka, Kyoto University) and TkDN4-M) established using the three genes (OCT3/4, SOX2, KLF-4) other than c-MYC, and human ES cells (KhES-3 (provided by Prof. Norio Nakatsuji, Kyoto University)) were compared (FIG. 1). On day 15 of culture from the iPS cells and the ES cells, hematopoietic progenitor cells extracted from a net-like structure were seeded onto feeder cells, and cultured in IMDM to which FBS in a final concentration of 15% was added, in the presence of TPO (100 ng/ml), SCF (50 ng/ml), and heparin (25 U/ml). The number of CD42b-positive megakaryocytic cells subsequently induced was counted over time (FIG. 1). As a result, the number of megakaryocytic cells increased in all three cell lines of the four-factor iPS cells (with c-MYC), as compared with the three-factor iPS cells (without c-MYC) and the human ES cells.

Figure 2:
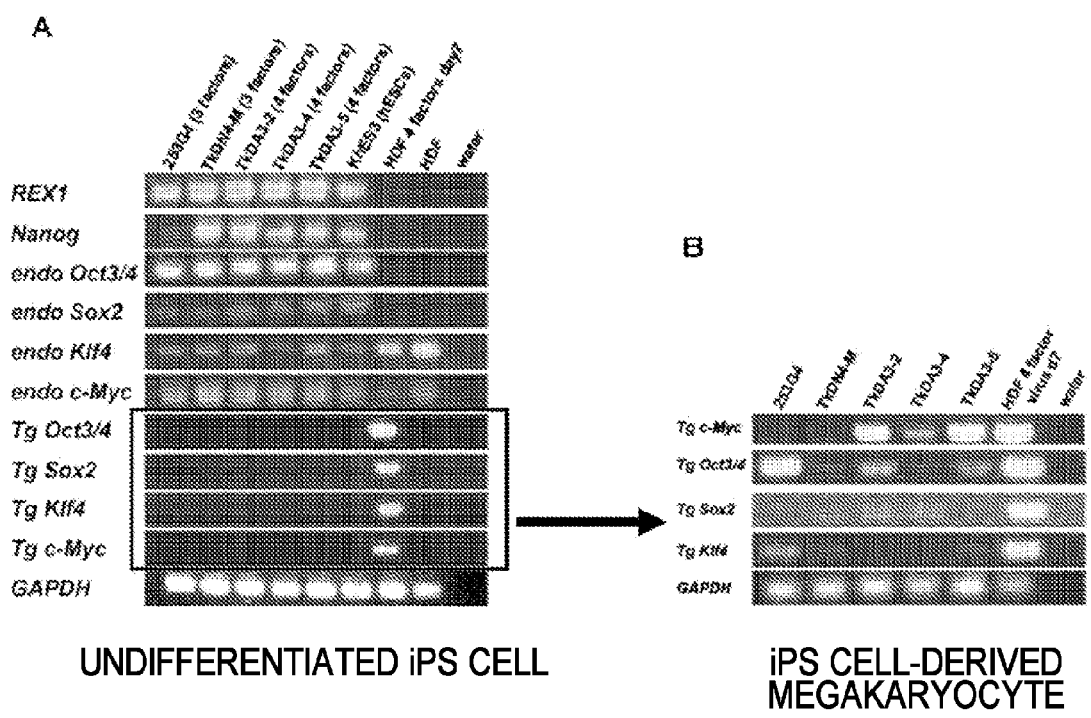
FIG. 2 is a view for confirming reactivation of transgenes in human iPS cell-derived megakaryocytic cells. Expression of each transgene (OCT3/4, SOX2, KLF-4, c-MYC) in four-factor iPS cells (TkDA3-2, TkDA3-4, and TkDA3-5) and three-factor iPS cells (TkDN4-M) was examined for undifferentiated iPS cells and differentiated megakaryocytic cells. Expression of each gene introduced into human dermal fibroblasts (HDF) as a gene introduction control was also examined. "endo" indicates an endogenous gene, and "Tg" indicates a transgene. Expression of REX1 and NANOG was also examined for undifferentiated iPS cells.

Next, the activation of the expression of the genes (OCT3/4, SOX2, KLF-4, c-MYC), which were introduced when producing the iPS cells, in undifferentiated iPS cells was examined. The examination showed that the expression of all genes was suppressed by a silencing mechanism (FIG. 2A). In differentiation-induced megakaryocytic cells on day 25 of culture, on the other hand, the reactivation of the expression of each transgene was confirmed (FIG. 2B).

Figure 3:
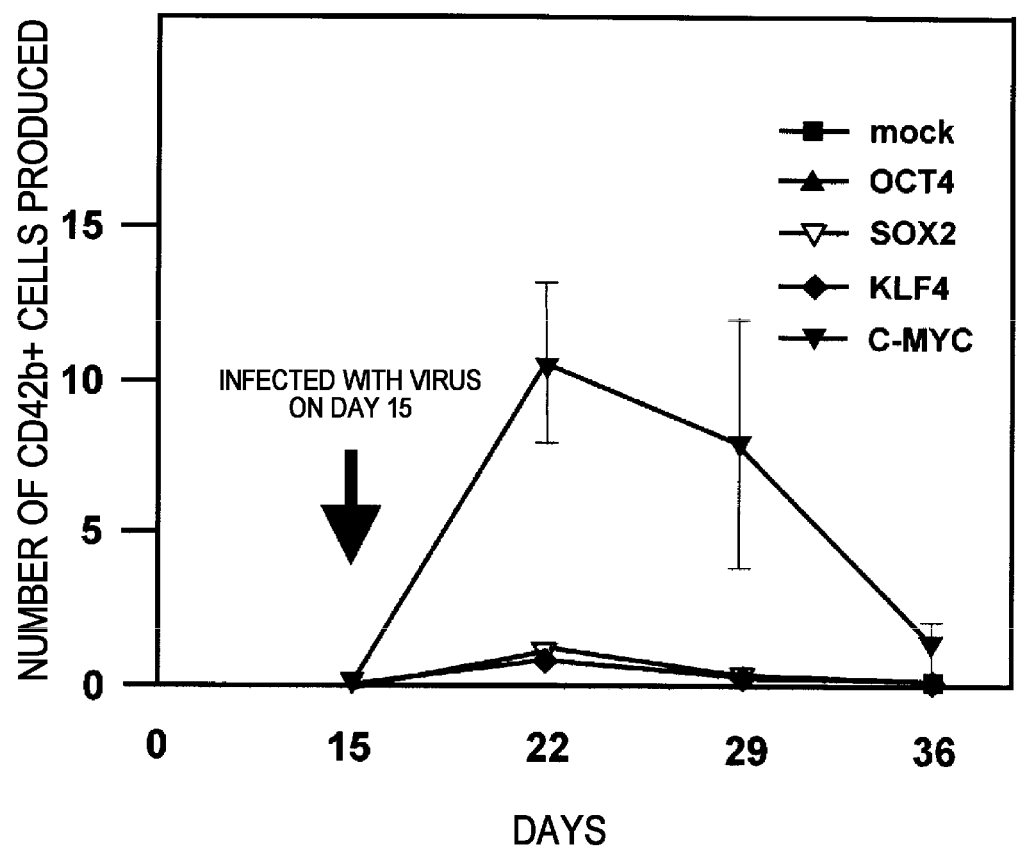
FIG. 3 shows an increase in the number of megakaryocytic cells by forced expression of c-MYC in ES cell-derived hematopoietic progenitor cells. Blood progenitor cells were extracted from a net-like structure on day 15 of culture of human ES cells, the genes (OCT3/4, SOX2, KLF-4, c-MYC) were each separately introduced into the blood progenitor cells, and the number of megakaryocytic cells subsequently produced was counted over time. The vertical axis represents the number of CD42b-positive megakaryocytic cells derived from each cell, where the number of CD42b-positive megakaryocytic cells derived from hematopoietic progenitor cells (mock) into which only a viral vector was introduced is set to 1. The horizontal axis represents the number of days after initiation of culture of ES cells.

These results suggest a possibility that the reactivation of the expression of any of the genes introduced when producing the iPS cells is related to the increase in the number of megakaryocytic cells produced. In view of this, the causal gene related to the increase in the number of megakaryocytic cells was investigated. Each gene was separately forcibly expressed by a retrovirus in hematopoietic progenitor cells derived from human ES cells (into which OCT3/4, SOX2, KLF-4, and c-MYC were not exogenously introduced, unlike the iPS cells), and the number of CD42b-positive megakaryocytic cells produced was counted. As a result, it was revealed that the number of CD42b-positive megakaryocytic cells produced increased by approximately 10 times in the case of introducing c-MYC, as compared with in the case of introducing the other genes (FIG. 3). These results indicate that the high megakaryocyte induction efficiency from the four-factor iPS cells can be attributed to the reactivation of the expression of the c-MYC gene.

It was also confirmed that the megakaryocytic cells induced from the four-factor iPS cells exhibited a higher survival rate after freeze-thawing, than the megakaryocytic cells induced from the ES cells or the three-factor iPS cells. In detail, while the survival rates after freeze-thawing of the megakaryocytic cells induced from the human ES cells (KhES-3) and the three-factor human iPS cells (TkDN4-M) were respectively 56.7% and 54.5%, i.e. merely approximately ½, the survival rate after freeze-thawing of the megakaryocytic cells induced from the four-factor human iPS cells (TkDA3-4) was 81.0%, reaching approximately ⅘. This indicates that the megakaryocytic progenitor cells in which the reactivation of the oncogene such as the c-MYC gene occurs are more suitable for cryopreservation, and are more easily supplied after thawing.

Figure 4:
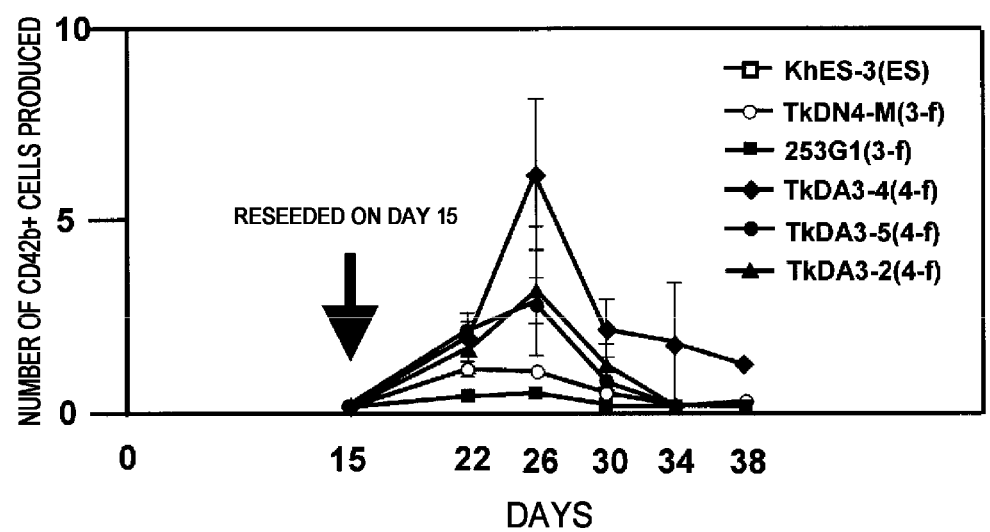
FIG. 4 is a graph for comparison of the numbers of platelets produced from four-factor iPS cells and three-factor iPS cells. The vertical axis represents the number of platelets derived from each cell, where the number of ES cell-derived platelets on day 21 of culture is set to 1. The horizontal axis represents the number of days after initiation of culture of iPS cells and ES cells. "3-f" indicates a three-factor iPS cell-derived cell line, "4-f" indicates a four-factor iPS cell-derived cell line, and "ES" indicates ES cells.

The number of platelets produced was studied in the same way as megakaryocytic cells. On day 15 of culture from the iPS cells and the ES cells, hematopoietic progenitor cells extracted from a net-like structure were seeded, and the number of platelets subsequently induced was counted over time. As a result, platelets were efficiently produced from the four-factor iPS cells, as in the case of megakaryocytic cells (FIG. 4).

Figure 5:
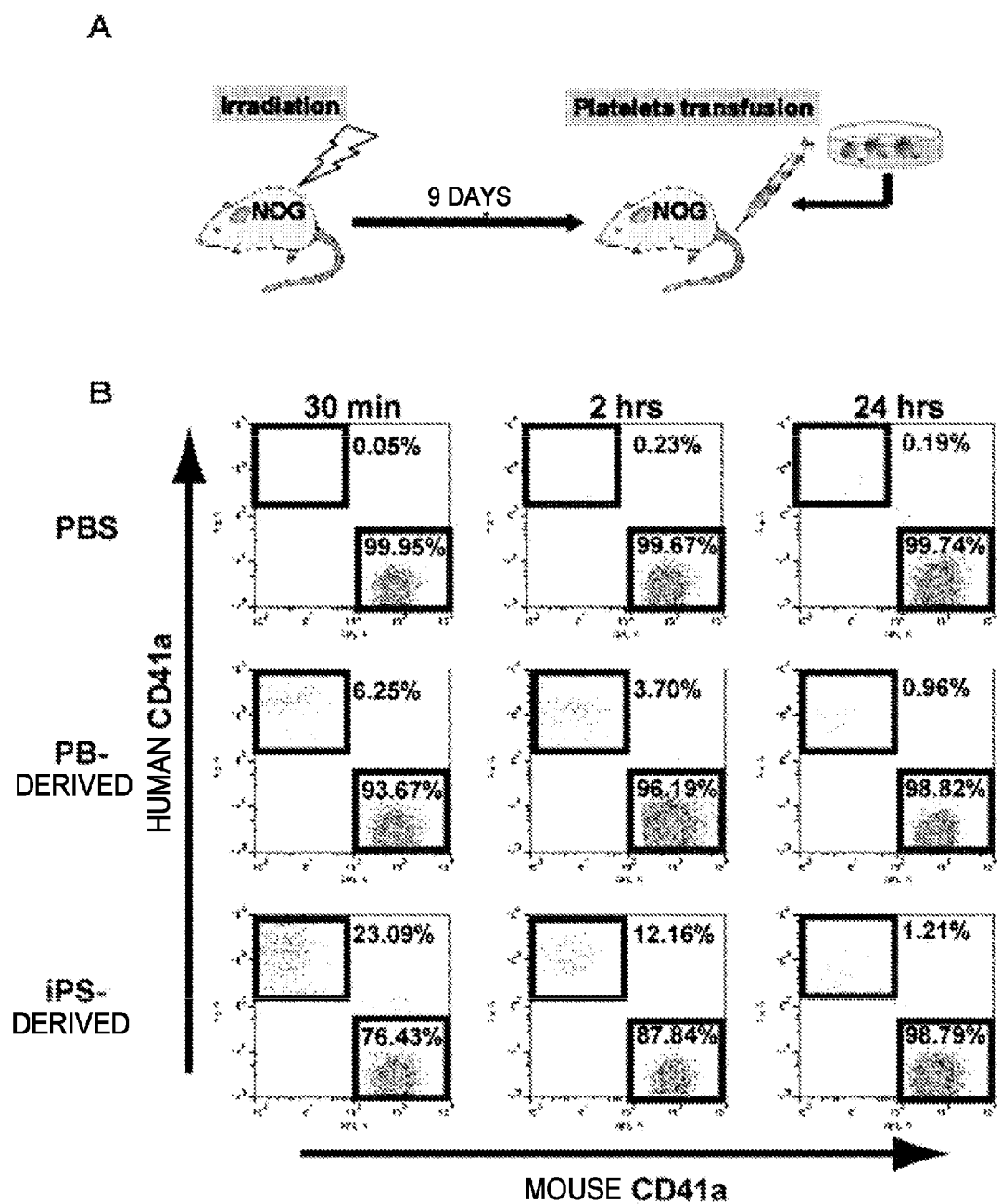
FIG. 5 shows an experiment of transfusion into a mouse model using iPS cell-derived platelets. Immunity-deficient mice of a thrombocytopenia model were provided by irradiation beforehand (A). Platelets produced from a TkDA3-4 cell line were transfused via the tail vein of the immunity-deficient mice. B shows time-dependent changes after the transfusion (30 minutes, 2 hours, 24 hours). "PB" indicates human peripheral blood.

Next, an experiment of transfusing platelets produced in vitro was conducted using the TkDA3-4 cell line having highest platelet production ability. Immunity-deficient mice of a thrombocytopenia model were provided by irradiation beforehand, and the iPS cell-derived platelets were transfused via the tail vein (FIG. 5A). Platelet chimerism of approximately 20% was observed 30 minutes after transfusion. Even 2 hours after transfusion, platelet chimerism of approximately 10% was still observed. Thus, the same characteristics as fresh platelets derived from human peripheral blood were exhibited (FIG. 5B).

Furthermore, thrombus formation ability of human iPS cell-derived platelets in vivo was evaluated by time-lapse confocal microscopy.

The iPS cell-derived platelets were stained with tetramethylrhodamine ethyl ester (TMRE: red pigment), mixed with hematoporphyrin, and injected via the tail vein of mice. By staining bloodstream (other than cell components) with FITC-dextran (green), blood components in the blood vessel were decolorized, allowing blood cell components to be recognized from their shape and size. When hematoporphyrin reacted by laser and vascular endothelial damage was caused, the platelets formed a solid layer and adhered to the damaged endothelium or the endothelial denudation spot, inducing thrombus formation.

Figure 6:
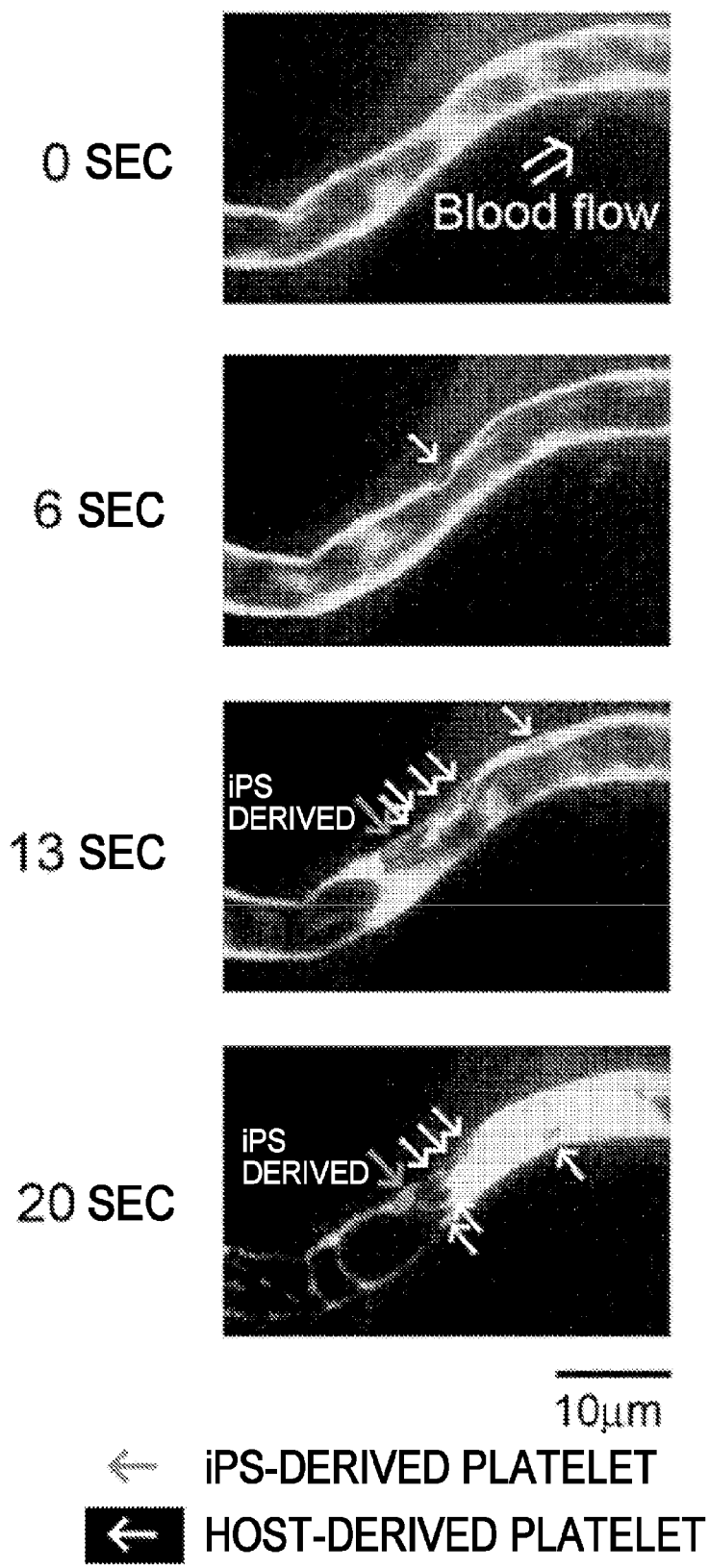
FIG. 6 is a view for confirming thrombus formation ability of human iPS cell-derived platelets in vivo. Human iPS cell-derived platelets were stained with tetramethylrhodamine ethyl ester (TMRE: red pigment), mixed with hematoporphyrin, and injected via the tail vein of mice. A thrombus formation state in the blood vessel 0 second, 6 seconds, 13 seconds, and 20 seconds after irradiating the mesenteric artery with laser was observed by time-lapse confocal microscopy. "Blood flow" indicates bloodstream.

The mesenteric small artery of the mice was irradiated with laser of a wavelength of 488 nm at 30 mW. After 13 seconds, the red-stained iPS cell-derived platelets adhered to the damaged endothelium (the area indicated as "iPS-derived" by the arrows in FIG. 6). After 20 seconds, the platelets induced thrombus formation in coordination with other host-derived platelets (mouse platelets), leading to blood vessel occlusion. Thus, the iPS cell-derived platelets were proved to be capable of thrombus formation in bloodstream in vivo.

These results demonstrate that platelets prepared from iPS cells which are established by introduction of the four genes including the c-MYC gene and in which the c-MYC gene is reactivated possess the same physiological characteristics as human peripheral blood-derived platelets.

As evident from the above analysis, in order to efficiently induce megakaryocytic cells and platelets from iPS cells, it is important to induce the expression of the c-MYC gene and maintain the effect of the c-MYC gene product in the cells. It is therefore expected that an effective way to induce megakaryocytic cells and platelets from iPS cells is to express the c-MYC gene in mononuclear megakaryocytic progenitor cells which are undifferentiated megakaryocytic progenitor cells and also suppress oncogene-induced senescence (OIS) in order to maintain the effect of the c-MYC gene product. In view of this, the polycomb gene was expressed simultaneously with the c-MYC gene for OIS suppression, and its effect was examined.

2. Mature Megakaryocytic Cell Production Efficiency from Megakaryocytic Progenitor Cells Expressing the c-Myc Gene and the BMI1 Gene As a result of the comparison of the megakaryocytic production efficiency between the iPS cell line established using the four genes and the iPS cell line established using the three genes, the reactivation of the c-MYC gene in the megakaryocytic progenitor cells was found to influence the number of mature megakaryocytic cells subsequently induced. Hence, how the expression of the c-MYC gene in megakaryocytic progenitor cells derived from ES cells which are pluripotent stem cells into which the c-MYC gene is not introduced influences subsequent induction of megakaryocytic cells was studied.

Figure 7:
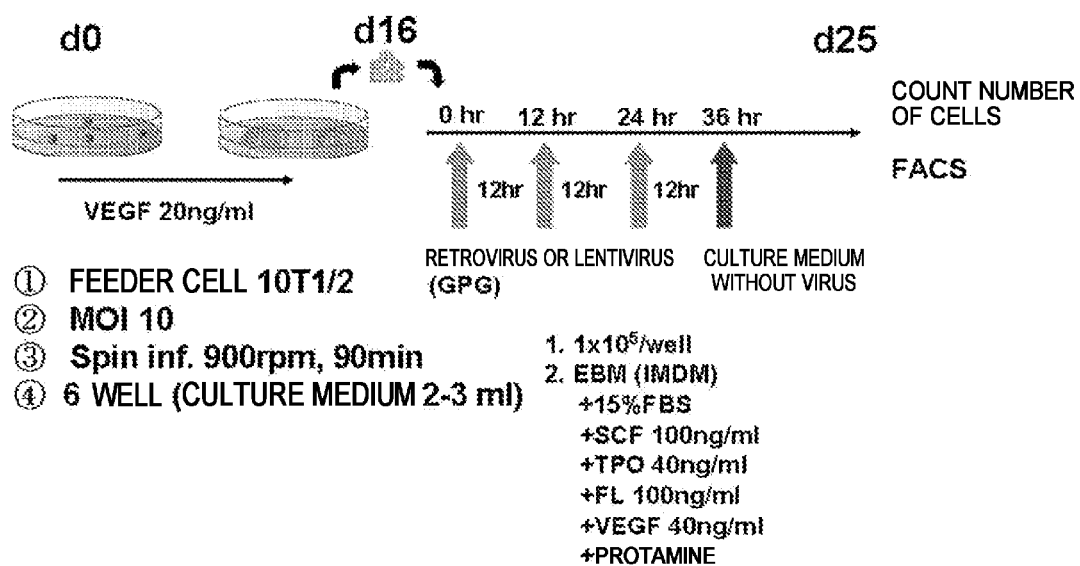
FIG. 7 schematically shows a protocol of introducing genes into hematopoietic progenitor cells prepared from ES cells.

A net-like structure was prepared from a human ES cell line (KhES-3) in the presence of 20 ng/ml VEGF. Megakaryocytic progenitor cells (pre-multinucleation) extracted from this net-like structure were seeded onto 10T1/2 cells to a concentration of $1\times10^5$ cells/well and, after 0 hour, 12 hours, and 24 hours from seeding, infected with a retroviral vector holding the c-MYC gene (SEQ ID NO: 1). After 36 hours, the culture medium was changed to a medium not containing the retrovirus, and the culture was continued. The gene introduction by the retrovirus was carried out by spin infection using a 6-well plate to which 2 to 3 ml culture medium was added, under conditions of 900 rpm and 90 minutes. The culture was performed using the culture medium in which 100 ng/ml SCF, 40 ng/ml TPO, 100 ng/ml FL, 40 ng/ml VEGF, and protamine were further added to IMDM to which FBS in a final concentration of 15% was added (FIG. 7).

Figure 8:
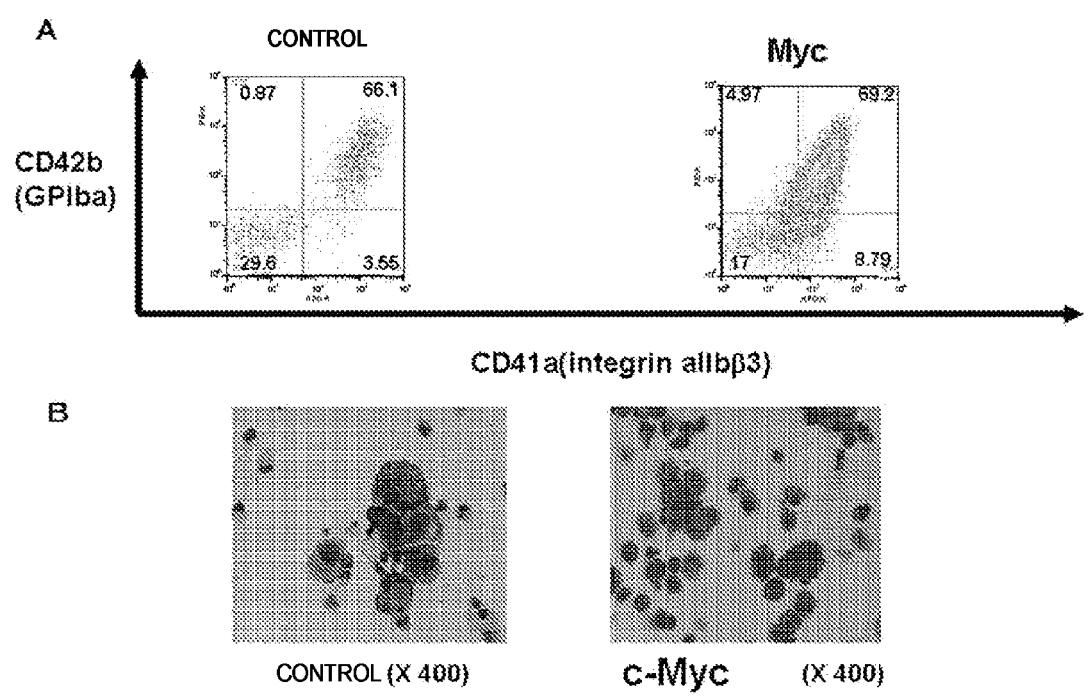
FIG. 8 shows FACS analysis results on day 9 after introducing the c-MYC gene into hematopoietic progenitor cells prepared from ES cells. A shows FACS analysis results, and B shows photomicrographs of the cells on day 9 after the c-MYC introduction. Cells into which only a MYC viral vector was introduced were used as a control.

As a result of FACS analysis on day 9 after retroviral infection, it was observed that cells having CD41a and CD42b dominantly increased in the cells into which c-MYC was introduced, as compared with a control vector (FIG. 8A). Moreover, when inspecting the cells by a cytospin, multinucleated cells were observed in the control, whereas pre-multinucleation mononuclear cells were observed in the c-MYC introduced cells (FIG. 8B). These results suggest that the forced expression of c-MYC causes mononuclear immature megakaryocytic cells to increase. The results are similar to those of transgenic mice in which c-MYC was expressed in a megakaryocyte-specific manner (see Alexander et al., Deregulated expression of c-MYC in megakaryocytes of transgenic mice increases megakaryopoiesis and decreases polyploidization, J. Biol. Chem., 1996 Sep. 20; 271 (38): 22976-82).

Figure 9:
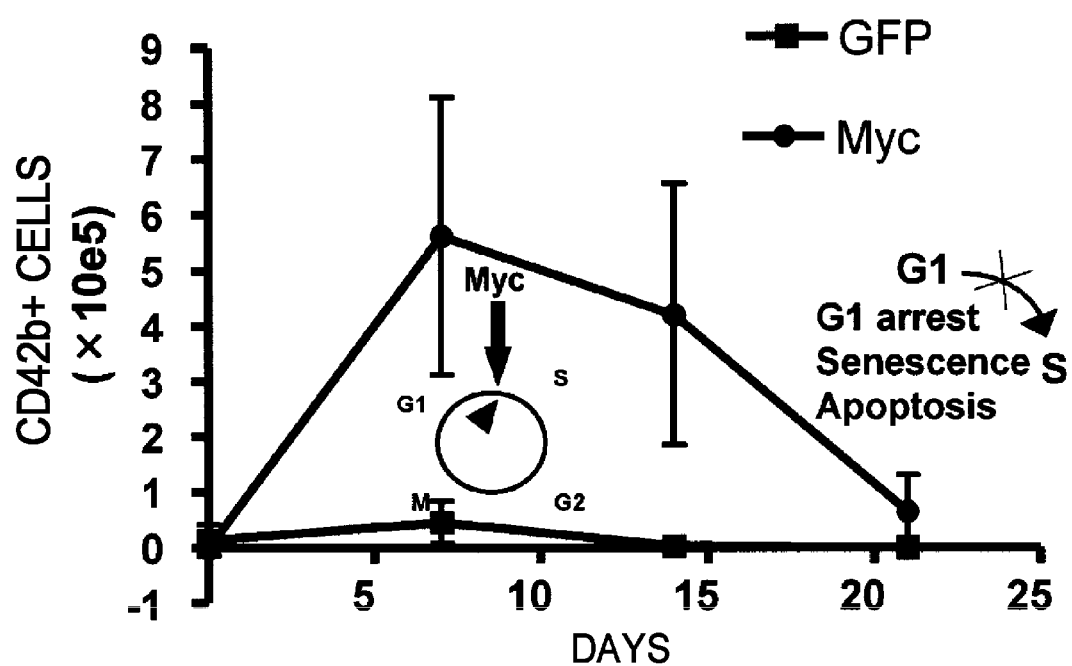
FIG. 9 shows growth ability of megakaryocytic progenitor cells expressing the c-MYC gene. The vertical axis represents the number of CD42b-positive cells. The horizontal axis represents the number of days after introducing the c-MYC gene into cells. ■ indicates results of a control into which only a viral vector was introduced instead of c-MYC.
Figure 10:
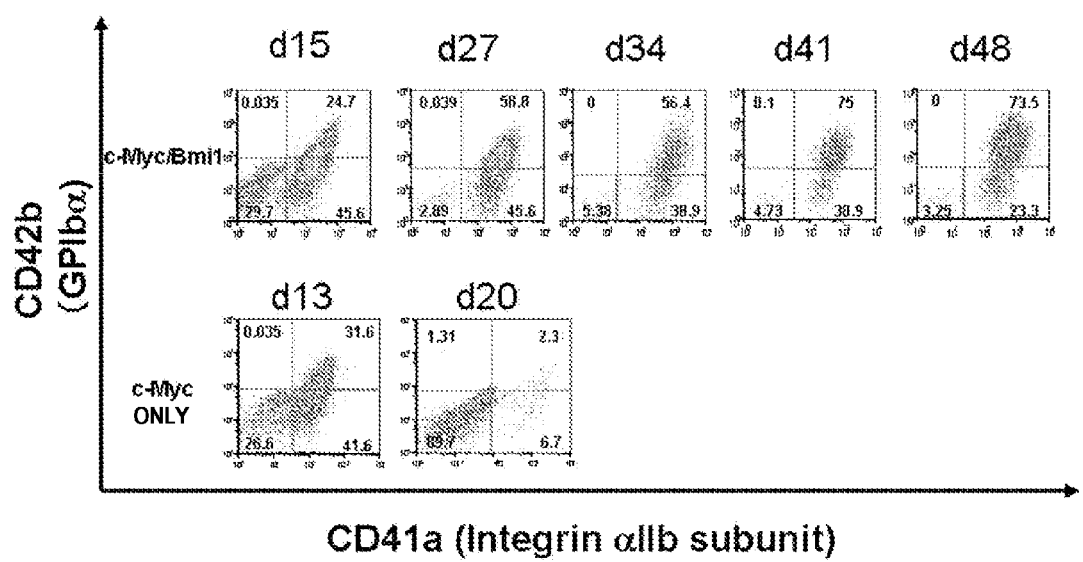
FIG. 10 shows FACS analysis results of megakaryocytic progenitor cells into which the c-MYC gene and the BMI1 gene were introduced. c-MYC/BMI1 (upper view) shows FACS analysis results of cells into which both the c-MYC gene and the BMI1 gene were introduced, whereas c-MYC only (lower view) shows FACS analysis results of cells into which only the c-MYC gene was introduced.
Figure 11:
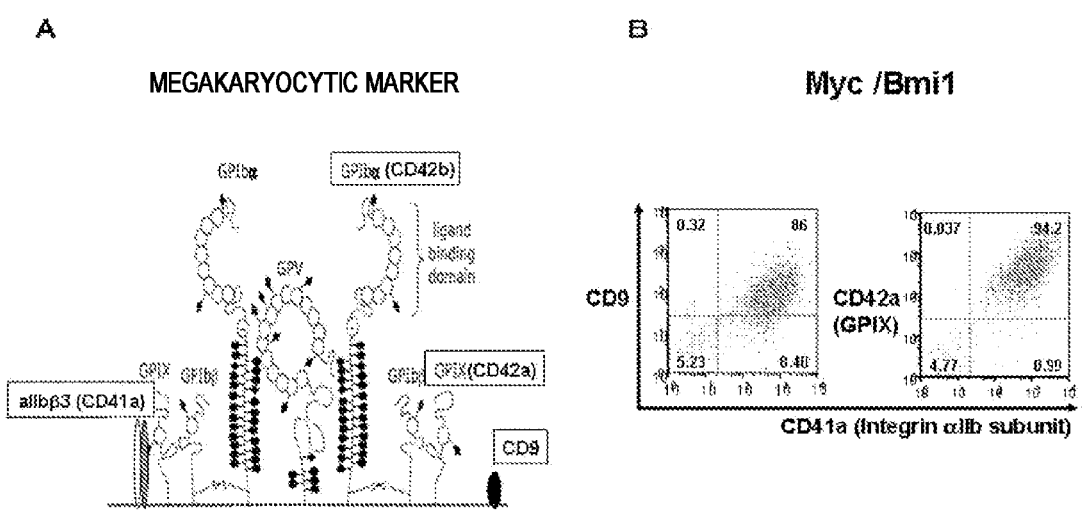
FIG. 11 shows FACS analysis results of cells on day 35 of culture, into which the c-MYC gene and the BMI1 gene were introduced. A schematically shows specific functional molecules of megakaryocytes, and B shows FACS analysis results.

Next, the cell growth ability in the c-MYC expressed state was inspected. As a result, the growth was observed to decrease from day 14 after infection (FIG. 9). This phenomenon is a cell canceration avoidance mechanism of effecting cell cycle arrest, senescence, and apoptosis in response to an abnormal growth signal due to excessive expression of an oncogene such as c-MYC, and is referred to as oncogene-induced senescence (OIS) (described above). In view of this, in an attempt to avoid OIS, BMI1 which is one of the polycomb genes for negatively regulating the Ink4a/Arf gene coding the tumor suppressor gene products p16 and p19 was introduced into the megakaryocytic progenitor cells. The c-MYC gene and the BMI1 gene (SEQ ID NO: 2) were introduced into the cells by the above-mentioned retroviral gene introduction method and expressed, after which FACS analysis was conducted. As a result, a CD41a-positive/CD42b-positive (megakaryocytic marker) cell colony stably and exponentially growing with time after gene introduction was obtained (FIG. 10). It was confirmed that, while the number of CD41a-positive/CD42b-positive cells significantly decreased on day 20 after gene introduction in the case of introducing only the c-MYC gene into the cells (lower analysis result in FIG. 10), the number of CD41a-positive/CD42b-positive cells increased day by day in the case of introducing the c-MYC gene and the BMI1 gene (upper analysis result in FIG. 10). This demonstrates that the megakaryocytic progenitor cells without multi-polyploidization into which not only the c-MYC gene is introduced but also the BMI1 gene as one of the polycomb genes is introduced are differentiated into megakaryocytic progenitor cells while retaining high growth ability by avoiding OIS. Here, in order to determine the characteristics of the obtained megakaryocytic cells, FACS analysis was conducted on whether or not CD9 and CD42a which are other megakaryocyte-specific functional molecules are present on the cell surfaces (see FIG. 11A). As a result, the presence of CD9 and CD42a in the cell line into which the c-MYC gene and the BMI1 gene were introduced was able to be confirmed (FIG. 11B).

Figure 12:
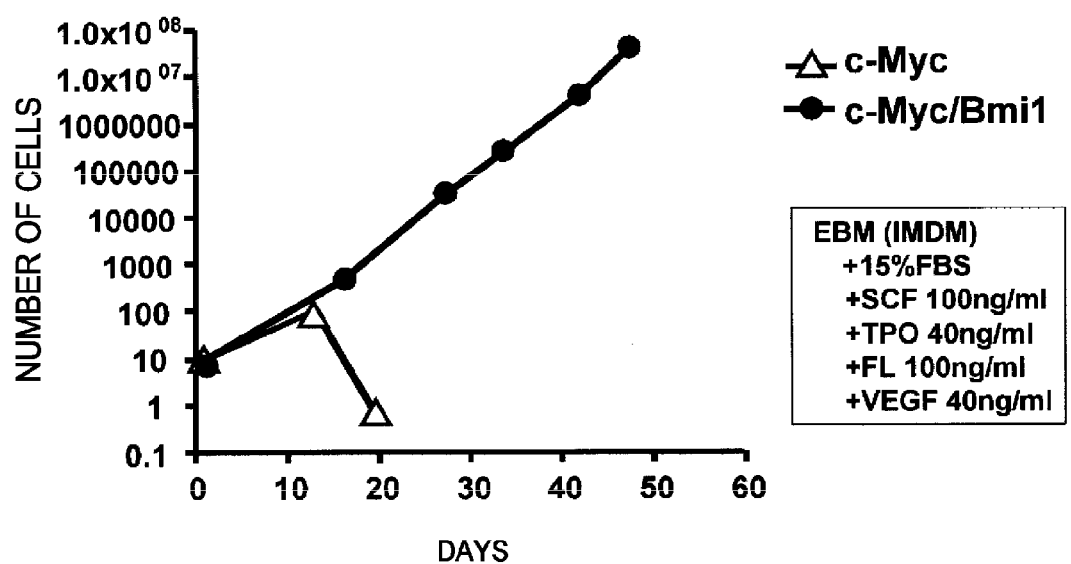
FIG. 12 shows results of examining growth ability of MYC/BMI1-expressing cells. The vertical axis represents the number of cells. The horizontal axis represents the number of days after introducing the genes into cells.
Figure 13:
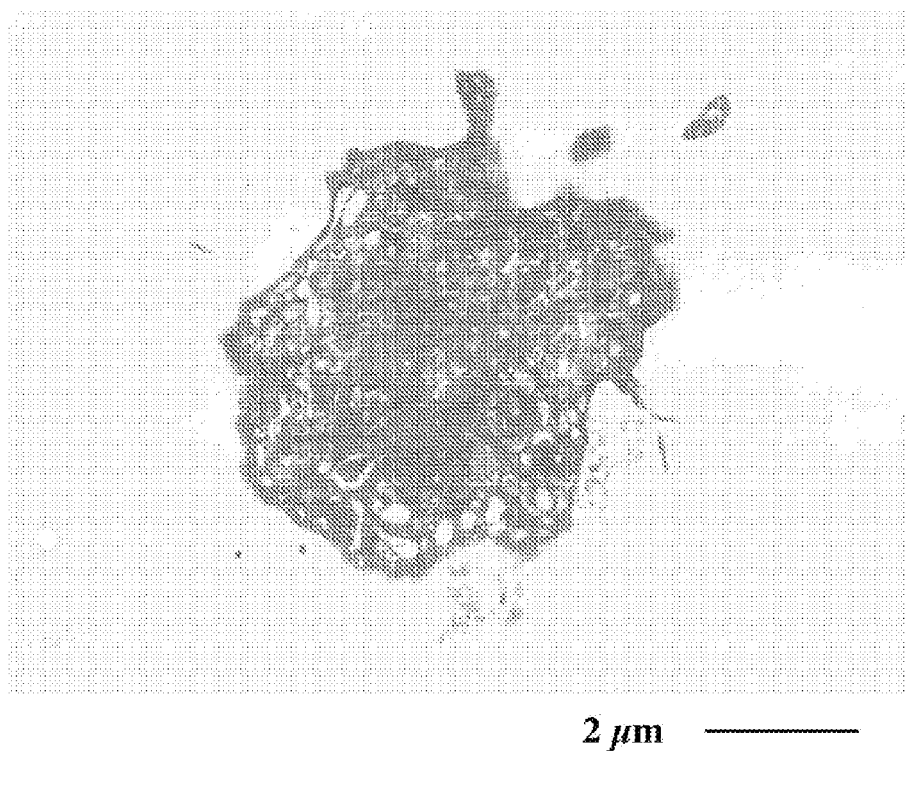
FIG. 13 shows an image of platelets released from megakaryocytic progenitor cells derived from c-MYC/BMI1-expressing cells, as observed through an electron microscope.

Next, the growth ability of the c-MYC/BMI1 expressing cells was examined. Megakaryocytic progenitor cells without multi-polyploidization into which the c-MYC gene and the BMI1 gene were introduced were cultured in a culture medium in which 100 ng/ml SCF, 40 ng/ml TPO, 100 ng/ml FL, and 40 ng/ml VEGF were further added to IMDM to which FBS in a final concentration of 15% was added, and the number of cells was counted over time. As a result, approximately $4\times10^7$ CD41a-positive cells were obtained on day 49 after gene introduction (FIG. 12). Besides, when observing platelets released from the megakaryocytic progenitor cells derived from the c-MYC/BMI1 expressing cells through an electron microscope, microtubular structures, open canalicular systems, and platelet granules characteristic of platelets were able to be confirmed (FIG. 13).

Figure 14:
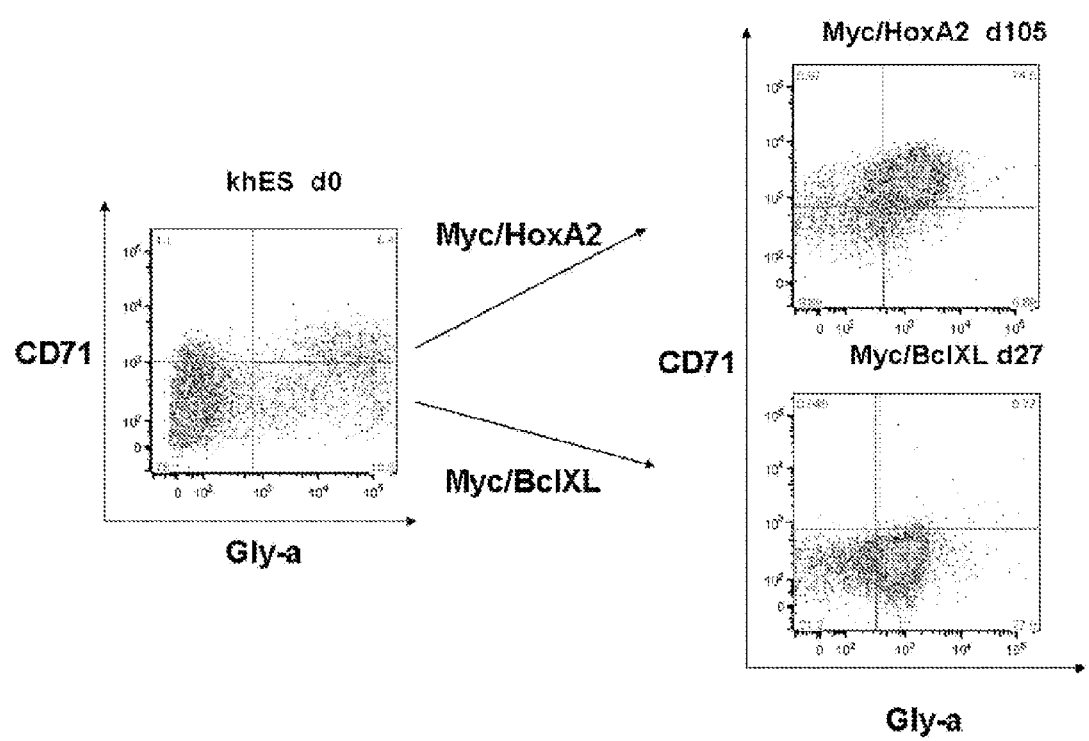
FIG. 14 shows FACS analysis results of cells on day 105 after introducing the c-MYC gene and the HOXA2 gene into ES cell (KhES)-derived hematopoietic progenitor cells, and on day 27 after introducing the c-MYC gene and the BCLXL gene into ES cell (KhES)-derived hematopoietic progenitor cells.

3. Erythrocyte Induction from c-Myc Gene-Introduced Hematopoietic Progenitor Cells Via Erythroid Progenitor Cells Next, erythrocyte production from erythroid progenitor cells obtained from hematopoietic progenitor cells into which the c-MYC gene was introduced was attempted. In the same way as the introduction of the c-MYC gene or the BMI1 gene described in the above section 2, c-MYC/HOXA2 (SEQ ID NO: 3) expressing cells and c-MYC/BCLXL (SEQ ID NO: 4) expressing cells were produced and FACS analysis was conducted. As a result, the presence of an erythroid marker CD71-positive/GlyA-positive cell colony in the c-MYC/HOXA2 expressing cells was confirmed on day 105 after gene introduction (upper right view in FIG. 14). Moreover, the presence of a GlyA-positive cell colony in the c-MYC/BCLXL expressing cells was also confirmed (lower right view in FIG. 14). This demonstrates that the hematopoietic progenitor cells into which the c-MYC gene is introduced can also be differentiated into erythrocytes by changing the combination of introduced factors.

4. Functional Platelet Production Using Gene Expression Induction System

As evident from above, an effective way to prepare megakaryocytic cells and platelets efficiently in large amount is to increase the number of megakaryocytic progenitor cells. To do so, it is necessary to co-express the c-MYC family gene and the polycomb gene simultaneously in megakaryocytic progenitor cells without multi-polyploidization to thereby enhance the growth ability of the megakaryocytic progenitor cells without multi-polyploidization. In order to facilitate megakaryocytic cell maturation (multinucleation), however, it is desirable to suppressively regulate the expression of the c-MYC family gene and the polycomb gene according to circumstances.

In view of this, platelets were produced by inducibly regulating the expression of the c-MYC gene and the BMI1 gene using a pMX tet off system, and the physiological functionality of the platelets was examined.

4-1. Confirmation of Functionality of Gene Regulation Vector

An all-in-one vector in which c-MYC-2A-BMI1 was incorporated into a pMX tet off vector (provided by Prof. Hiroyuki Mano, Jichi Medical University) was prepared ("2A" is a peptide having self cleavage activity derived from the foot-and-mouth disease virus, where a plurality of proteins can be efficiently obtained from a single promoter by sandwiching this sequence between a plurality of proteins (Hasegawa et al., 2007 Stem Cells)). The pMX tet off c-MYC 2A BMI1 vector induces the expression of the c-MYC gene and the BMI1 gene in the presence of estradiol, and suppresses the expression of the c-MYC gene and the BMI1 gene in the presence of tetracycline and in the absence of estradiol.

Figure 15:
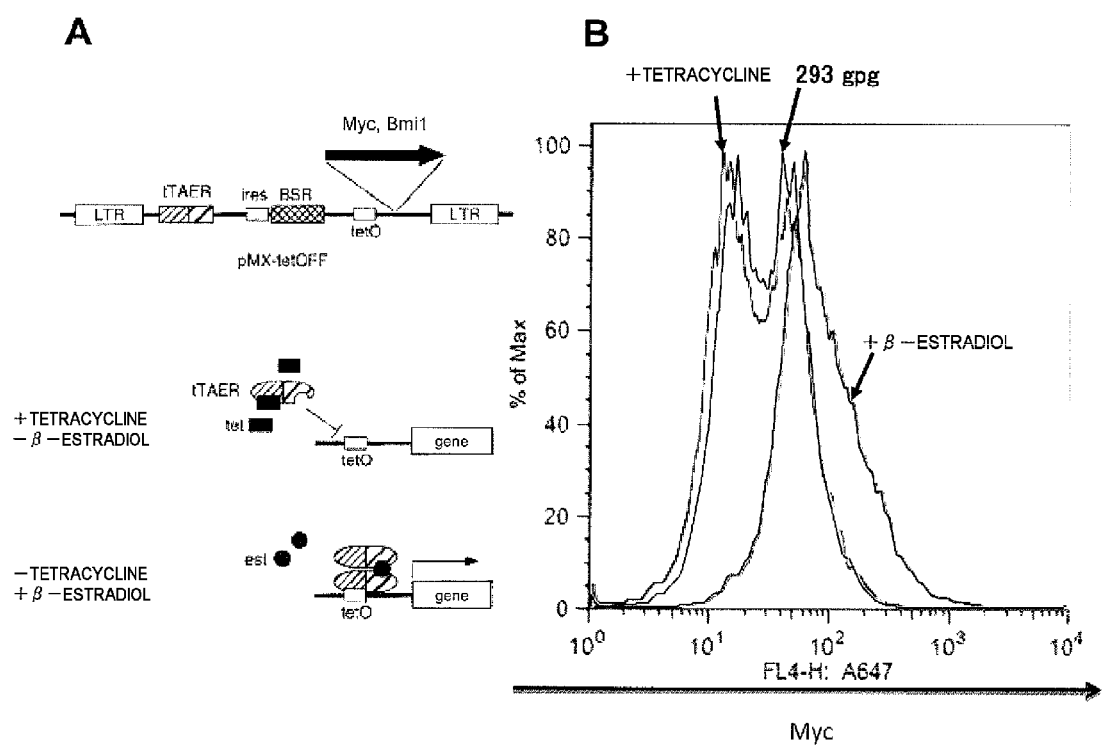
FIG. 15 is a view for confirming a gene expression regulation system by a pMX tet off vector. A construct in which c-MYC and BMI1 were linked to the pMX tet off vector with 2A in between was expressed in 293GPG cells to study whether or not the gene expression regulation functions. A shows the vector construct and mechanism, and B shows results of examining c-MYC expression in cells in a state where tetracycline and β-estradiol are added or not added, using a flow cytometer. The horizontal axis in B represents a c-MYC expression level. "293gpg" indicates results of 293GPG cells of a control.

The prepared pMX tet off c-MYC 2A BMI1 vector was expressed in 293GPG cells, and the expression regulation state of the c-MYC gene and the BMI1 gene was confirmed by FACS. FIG. 15 shows results of FACS analysis where c-MYC protein in the cells was stained with an anti-c-MYC protein antibody and then stained with an Alexa647-labeled secondary antibody. As can be understood from the drawing, in the 293GPG cells into which pMX tet off c-MYC 2A BMI1 was incorporated, the expression level of the c-MYC gene was similar to that in 293GPG cells of a control in the presence of tetracycline (the graphs indicated as 293gpg and +tetracycline in FIG. 15), but the expression of the c-MYC gene was stimulated in the presence of estradiol (the graph indicated as +β-estradiol in FIG. 15).

These results demonstrate that the expression of the target gene can be regulated by the pMX tet off c-MYC 2A BMI1 vector used here.

4-2. Megakaryocytic Cell Line Production by Gene Regulation Vector

The gene regulation vector described in the above section 4-1 was used to express the c-MYC gene and the BMI1 gene in megakaryocytic progenitor cells derived from a human ES cell line (KhES-3), and their growth ability and differentiation ability were examined.

Figure 16:
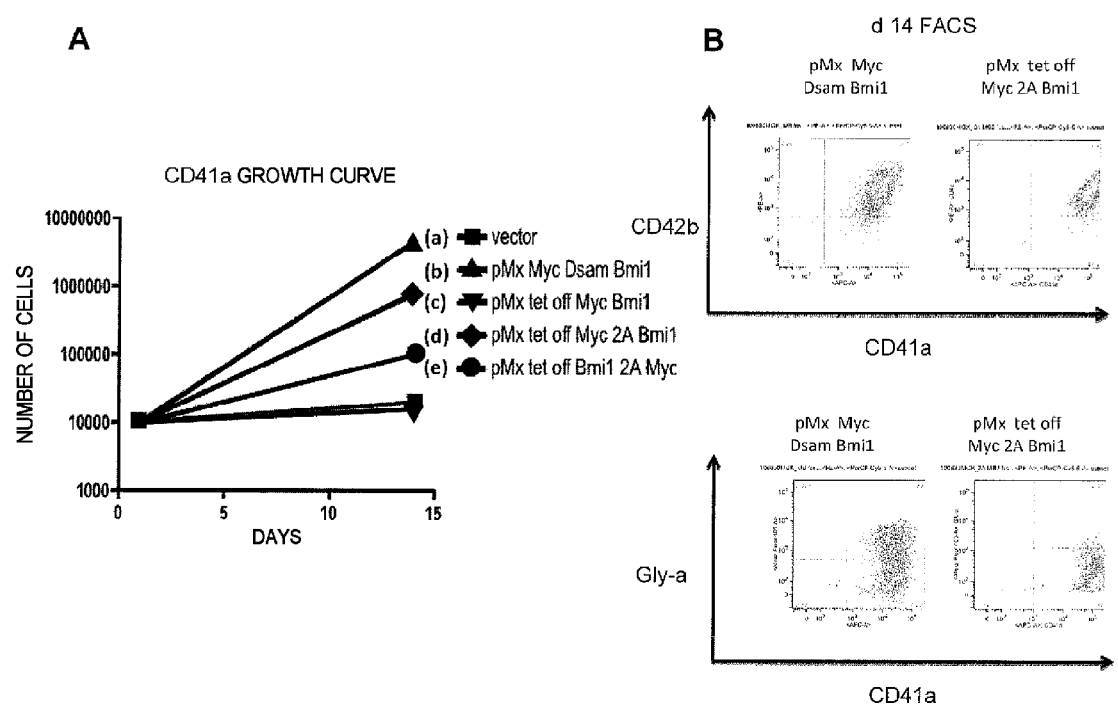
FIG. 16 shows results of studying growth ability and differentiation ability of gene regulation vector-expressing cell lines. A shows results of examining growth ability of cells expressing c-MYC and BMI1 by various vectors. The vertical axis represents the number of cells, and the horizontal axis represents the number of days after introducing the genes into cells. B shows results of analyzing cells stained with an anti-CD42b (GPIb-alpha) antibody and an anti-CD41a (Integrin alphaIIb/beta3 complex) antibody (upper view) and an anti-Glycophorin-a antibody and an anti-CD41a antibody (lower view), using a flow cytometer. In both the upper and lower views of B, results of cells forcibly expressing pMX c-MYC and Dsam BMI1 separately are shown on the left side, and results of cells expressing pMX tet off c-MYC 2A BMI1 are shown on the right side.

The examination was conducted on cells into which only a vector was introduced (FIG. 16A($a$)), a cell line in which pMX c-MYC and Dsam BMI1 were separately forcibly expressed (FIG. 16A($b$)), a cell line in which pMX tet off c-MYC and pMX tet off BMI1 were separately expressed (FIG. 16A($c$)), a cell line in which pMX tet off c-MYC 2A BMI1 was expressed (FIG. 16A($d$)), and a cell line in which pMX tet off BMI1 2A c-MYC was expressed (FIG. 16A($e$)). Here, ($d$) and ($e$) are constructs that differ in arrangement order of the c-MYC gene and the BMI1 gene with the 2A sequence in between.

FIG. 16A shows CD41a+ cell growth curves for these cell lines. Each cell line was stained with an anti-CD41a antibody and an anti-CD42b antibody as megakaryocytic markers, and analyzed using a flow cytometer. The cell line generated using pMX tet off c-MYC 2A BMI1 (FIG. 16A($d$)) shows the same phenotype as the cell line forcibly expressing pMX c-MYC and Dsam BMI1 separately (FIG. 16A($b$)), where most cell populations expressed the megakaryocytic marker (upper panel in FIG. 16B). Moreover, the cell line generated using pMX tet off c-MYC 2A BMI1 (FIG. 16A($d$)) exhibited higher growth ability than the cell line into which pMX tet off c-MYC and pMX tet off BMI1 were separately introduced (FIG. 16A($c$)) and the cell line generated using pMX tet off BMI1 2A c-MYC (FIG. 16A($e$)).

When stained with an anti-Glycophorin-a antibody and an anti-CD41a antibody, a megakaryocyte/erythroblast common marker CD41a+/Gly-a+ cell population was present in the cell line forcibly expressing pMX c-MYC and Dsam BMI1 separately (lower panel in FIG. 16B, left), whereas Gly-a disappeared in the cell line generated using pMX tet off c-MYC 2A BMI1 (lower panel in FIG. 16B, right). This indicates that the cell line generated using pMX tet off c-MYC 2A BMI1 is a cell line more differentiated into megakaryocytes than the cell line forcedly expressing pMX c-MYC and Dsam BMI1 separately.

4-3. Regarding Megakaryocyte Multinucleation

Figure 17:
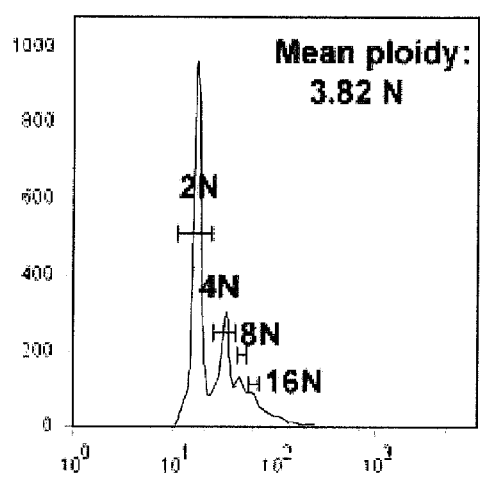
FIG. 17 shows study on the degree of multinucleation of a megakaryocytic cell line expressing pMX tet off c-MYC 2A BMI1 in the presence of β-estradiol. A shows results of cells of a control with only a vector (a cell line not expressing genes), and B shows results of cells expressing c-MYC and BMI1.
Figure 17:
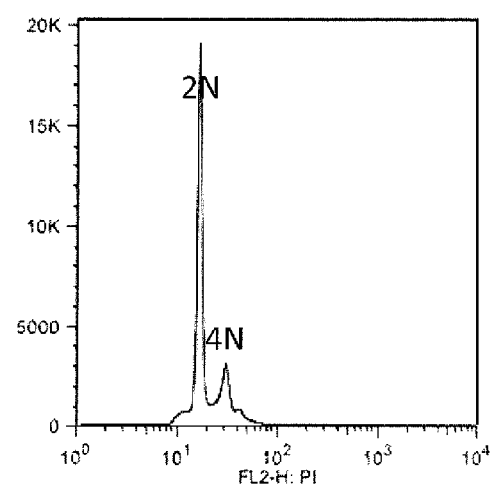

The degree of multinucleation of the cell line forcibly expressing the c-MYC gene and the BMI1 gene by the pMX tet off c-MYC 2A BMI1 vector in the presence of β-estradiol was examined. Human-derived megakaryocytes typically multinucleated to approximately 32 N (FIG. 17A). On the other hand, the cell line forcibly expressing the c-MYC gene and the BMI1 gene by the pMX tet off c-MYC 2A BMI1 vector hardly multinucleated, with the multinucleation degree of 2N to 4N.

4-4. Functional Analysis of Platelets Derived from Megakaryocytic Cell Line Expressing the c-Myc Gene and the BMI1 Gene Functional assays were performed on platelets derived from a megakaryocytic cell line expressing the c-MYC gene and the BMI1 gene.

Figure 18:
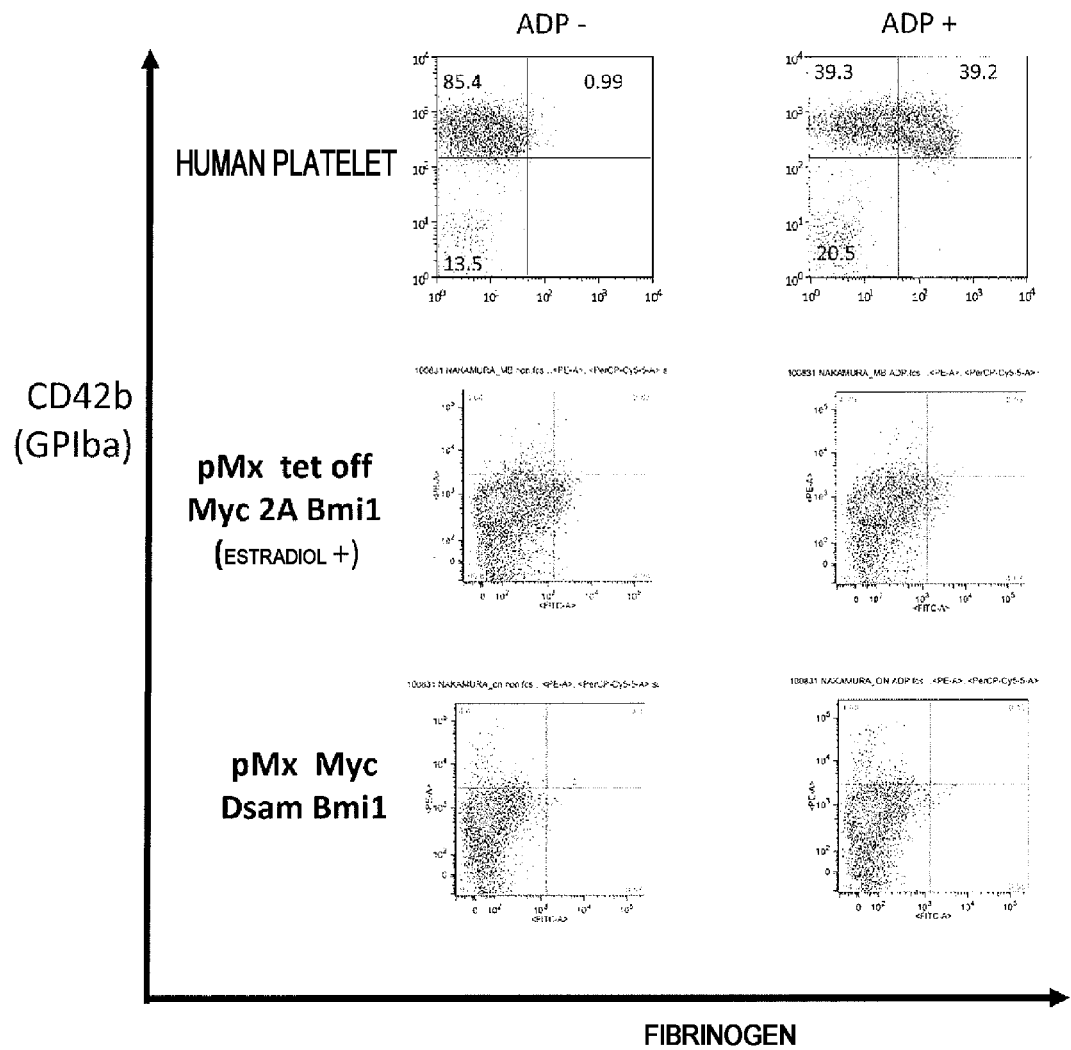
FIG. 18 shows results of performing fibrinogen-binding assays on platelets derived from megakaryocytes forcibly expressing c-MYC and BMI1. The upper view (human platelet) shows results of platelets derived from human peripheral blood, the middle view (pMX tet off c-MYC 2A BMI1) shows results of platelets derived from a pMX tet off c-MYC 2A BMI1 cell line in the presence of β-estradiol, and the lower view (pMx Myc Dsam Bmi1) shows results of platelets derived from a cell line forcibly expressing c-MYC and BMI1 by pMX c-MYC and Dsam BMI1.

Human peripheral blood-derived platelets of a control bound to fibrinogen in the presence of ADP (adenosine diphosphate, an intracellular factor for platelet activation), exhibiting normal integrin activation ability (inside-out signal) necessary for an initial stage of thrombus formation (upper right view in FIG. 18). Meanwhile, neither the pMX tet off c-MYC 2A BMI1 cell line (in the presence of estradiol) nor the pMX c-MYC and Dsam BMI1 forcibly expressing cell line bound to fibrinogen even when ADP was added (middle and lower views in FIG. 18). Thus, it was revealed that platelets having normal functionality are not released when the c-MYC gene and the BMI1 gene remain forcibly expressed.

Figure 19:
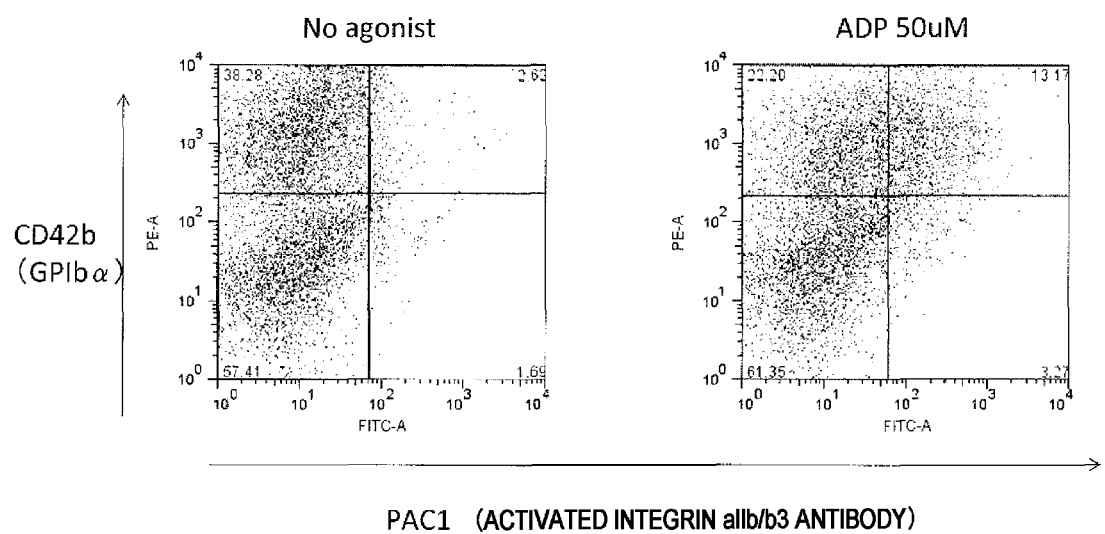
FIG. 19 shows results of examining integrin activation ability of platelets produced from a megakaryocytic cell line in which expression of c-MYC and BMI1 was suppressed. The left view shows analysis of integrin activation ability in the absence of ADP using a flow cytometer, whereas the right view shows analysis of integrin activation ability in the presence of ADP (50 μM) using a flow cytometer.

Next, for the cell line forcibly expressing the c-MYC gene and the BMI1 gene by the pMX tet off c-MYC 2A BMI1 vector, after turning off the forced expression under conditions of +tetracycline and −β-estradiol, the integrin activation ability of the CD41a+/CD42b+ platelets on day 4 of culture was analyzed using a flow cytometer (FIG. 19). As a result, it was found that a PAC1 antibody (activated integrin αIIbβ3 bound antibody) bound in the presence of ADP, exhibiting normal integrin activation ability (inside-out signal) (FIG. 19B).

These results indicate that, though platelets produced from a megakaryocytic cell line grown by forced expression of the c-MYC gene have functional disorder, platelets having normal functionality can be produced by turning off the forced expression of the c-MYC gene and the like in the megakaryocytic cell line.

The expression regulation of the c-MYC gene and the BMI1 gene in the megakaryocytic progenitor cells described above is also applicable to the MYC family gene, the BCLXL gene, and the HOXA2 gene used for establishing an erythroid progenitor cell line, enabling mature erythrocytes to be induced.

Figure 20:
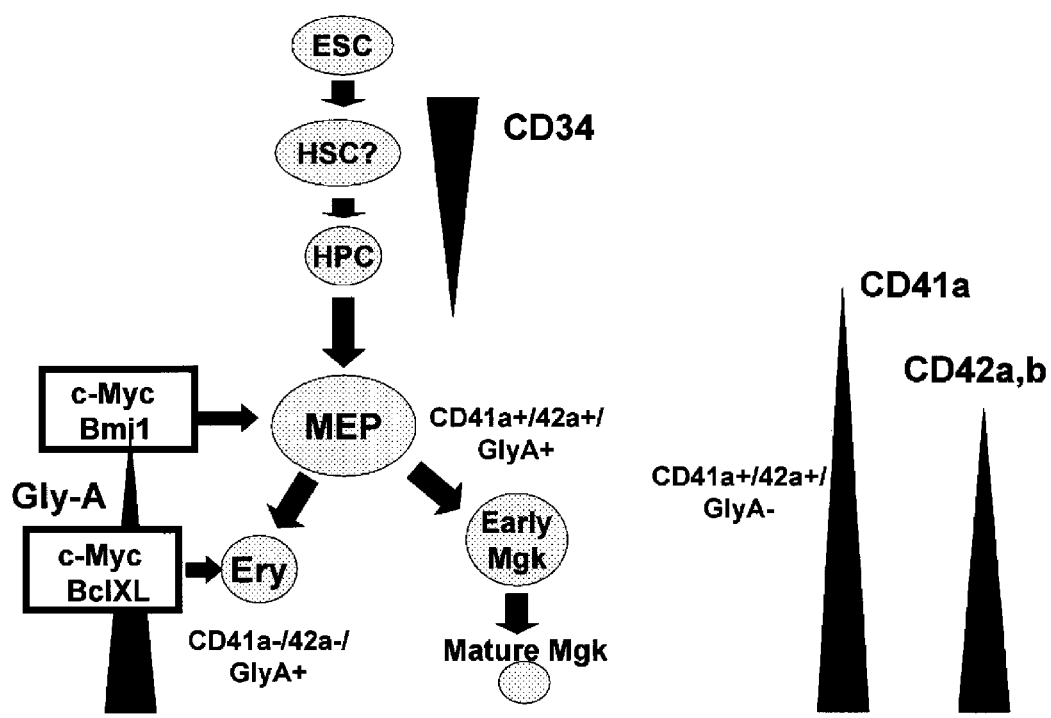
FIG. 20 shows a differentiation pathway from ES cells to a megakaryocytic cell line.

It was revealed that MYC and BMI1 cause cell growth in a stage of MEP fractions which are progenitor cells common to megakaryocytic cells and erythroid cells or in a stage of megakaryocytic progenitor cells more differentiated than MEP fractions (FIG. 20). Since megakaryocytic progenitor cells without multi-polyploidization into which the c-MYC gene and the BMI gene are introduced can be cryopreserved, megakaryocytic cells and platelets can be prepared from frozen stocks when necessary.

Likewise, an erythroid progenitor cell line produced by introducing the MYC gene and the BCLXL or HOXA2 gene can be cryopreserved, and thawed and prepared when necessary.

Furthermore, by upregulating or downregulating the expression of the introduced MYC gene and BMI1 gene, platelets or erythroid cells retaining bioactivity can be prepared in sufficient amount.

Industrial Applicability

The present invention provides a method of amplifying cells in a differentiation stage to produce more differentiated specific cells. By applying the method according to the present invention to, for example, blood cells, cells in a desired differentiation stage can be supplied in large amount. Hence, the present invention especially constitutes a significant contribution to development of treatment in the field of medicine.

---

The invention claimed is:

1. A method of producing mature megakaryocytic cells from megakaryocytic progenitor cells without polyploidization comprising:
   differentiating megakaryocytic progenitor cells without polyploidization by (i) inducing expression of an MYC family oncogene and polycomb complex protein-1 (BMI1)
   in the megakaryocytic progenitor cells without polyploidization; and (ii) culturing the cells.

2. The method according to claim 1, wherein the culturing comprises:
   culturing the cells by suppressing the expression of the MYC family oncogene and the BMI1; or
   culturing the cells after the MYC family oncogene and the BMI1 have been removed from the cells.

3. The method according to claim 1 further comprising cryopreserving the grown cells after the differentiating step, wherein the culturing is conducted after the cells are thawed.

4. A method of producing a platelet product comprising:
   producing mature megakaryocytic cells by the method according to any one of claims 1-3;
   recovering from the culture of the megakaryocytic cells a fraction of a culture solution in which platelets released from megakaryocytic cells are abundant; and
   removing blood cell components other than platelets from the fraction.

5. A method of producing a blood product comprising:
   producing a platelet product by the method according to claim 4; and
   mixing the platelet product with other components of a blood product.

6. The method according to claim 1, wherein the MYC family oncogene is c-MYC oncogene.

7. The method according to claim 4, wherein the MYC family oncogene is c-MYC oncogene.

8. The method according to claim 5, wherein the MYC family oncogene is c-MYC oncogene.

9. The method according to claim 2 further comprising cryopreserving the grown cells after the differentiating step, wherein the culturing is conducted after the cells are thawed.

10. A method of producing a platelet product comprising:
    producing mature megakaryocytic cells by the method according to claim 9;
    recovering from the culture of the megakaryocytic cells a fraction of a culture solution in which platelets released from megakaryocytic cells are abundant; and
    removing blood cell components other than platelets from the fraction.

11. A method of producing a blood product comprising:
    producing a platelet product by the method according to claim 10; and
    mixing the platelet product with other components of a blood product.

* * * * *